(12) United States Patent
Eckhardt et al.

(10) Patent No.: US 7,470,716 B2
(45) Date of Patent: Dec. 30, 2008

(54) IMIDAZOLES AND TRIAZOLES, THEIR PREPARATION, AND THEIR USE AS PHARMACEUTICAL COMPOSITIONS

(75) Inventors: Matthias Eckhardt, Biberach (DE); Frank Himmelsbach, Mittelbiberach (DE); Elke Langkopf, Warthausen (DE); Leo Thomas, Biberach (DE); Mohammad Tadayyon, Ulm (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 491 days.

(21) Appl. No.: 11/166,900

(22) Filed: Jun. 24, 2005

(65) Prior Publication Data
US 2006/0004074 A1    Jan. 5, 2006

Related U.S. Application Data

(60) Provisional application No. 60/590,019, filed on Jul. 21, 2004.

(30) Foreign Application Priority Data

Jun. 24, 2004    (DE)    ........................ 10 2004 030 502

(51) Int. Cl.
A61K 31/41    (2006.01)
A61K 31/415   (2006.01)
C07D 249/00   (2006.01)
C07D 233/00   (2006.01)

(52) U.S. Cl. .................... 514/383; 514/385; 548/262.2; 548/300.1

(58) Field of Classification Search ................. 514/383; 548/262.2
See application file for complete search history.

(56) References Cited

U.S. PATENT DOCUMENTS

| | | | |
|---|---|---|---|
| 2,928,833 A | 3/1960 | Leake et al. | |
| 4,005,208 A | 1/1977 | Bender | |
| 4,599,338 A | 7/1986 | Regnier et al. | |
| 5,041,448 A | 8/1991 | Janssens | |
| 5,051,517 A | 9/1991 | Findeisen et al. | |
| 5,223,499 A | 6/1993 | Greenlee | |
| 5,234,897 A | 8/1993 | Findeisen et al. | |
| 5,258,380 A | 11/1993 | Janssens | |
| 5,266,555 A | 11/1993 | Findeisen et al. | |
| 5,389,642 A | 2/1995 | Dorsch | |
| 5,470,579 A | 11/1995 | Bonte et al. | |
| 5,719,279 A | 2/1998 | Kuefner-Muhl et al. | |
| 5,753,635 A | 5/1998 | Buckman | |
| 6,303,661 B1 | 10/2001 | Demuth | |
| 6,342,601 B1 | 1/2002 | Bantick | |
| 6,548,481 B1 | 4/2003 | Demuth et al. | |
| 6,579,868 B1 | 6/2003 | Asano | |
| 6,784,195 B2 * | 8/2004 | Hale et al. | ................... 514/341 |
| 6,821,978 B2 | 11/2004 | Chackalamannil | |
| 6,869,947 B2 | 3/2005 | Kanstrup | |
| 7,060,722 B2 | 6/2006 | Kitajima | |
| 7,074,794 B2 | 7/2006 | Kitajima | |
| 7,074,798 B2 | 7/2006 | Yoshikawa | |
| 7,074,923 B2 | 7/2006 | Dahanukar | |
| 7,109,192 B2 | 9/2006 | Hauel | |
| 7,179,809 B2 | 2/2007 | Eckhardt | |
| 7,183,280 B2 | 2/2007 | Himmelsbach | |
| 7,192,952 B2 | 3/2007 | Kanstrup | |
| 7,217,711 B2 | 5/2007 | Eckhardt | |
| 7,235,538 B2 | 6/2007 | Kanstrup et al. | |
| 2002/0161001 A1 | 10/2002 | Kanstrup | |
| 2002/0169174 A1 | 11/2002 | Chackalamannil et al. | |
| 2002/0198205 A1 | 12/2002 | Himmelsbach | |
| 2003/0105077 A1 | 6/2003 | Kanstrup et al. | |
| 2003/0199528 A1 | 10/2003 | Kanstrup | |
| 2003/0232987 A1 | 12/2003 | Dahanukar et al. | |
| 2003/0236272 A1 | 12/2003 | Carr | |
| 2004/0034014 A1 | 2/2004 | Kanstrup et al. | |
| 2004/0077645 A1 | 4/2004 | Himmelsbach et al. | |
| 2004/0082570 A1 | 4/2004 | Yoshikawa | |
| 2004/0087587 A1 | 5/2004 | Himmelsbach | |
| 2004/0097510 A1 | 5/2004 | Himmelsbach et al. | |
| 2004/0116328 A1 | 6/2004 | Yoshikawa et al. | |
| 2004/0122228 A1 | 6/2004 | Maier | |

(Continued)

FOREIGN PATENT DOCUMENTS

CA    2136288 A1    5/1995

(Continued)

OTHER PUBLICATIONS

Patini et al., Chem. Rev., 1996, vol. 96, No. 8, pp. 3147-3176.*

(Continued)

Primary Examiner—Rei-tsang Shiao
Assistant Examiner—Susannah Chung
(74) Attorney, Agent, or Firm—Michael P. Morris; Mary-Ellen M. Devlin; David L. Kershner

(57) ABSTRACT

The present invention relates to imidazoles and triazoles of general formula

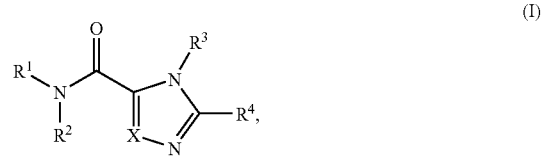

(I)

wherein $R^1$ to $R^4$ and X are defined as in claims 1 to 8, the tautomers, the enantiomers, the diastereomers, the mixtures thereof and the salts thereof, which have valuable pharmacological properties, particularly an inhibiting effect on the activity of the enzyme dipeptidylpeptidase-IV (DPP-IV).

17 Claims, No Drawings

U.S. PATENT DOCUMENTS

| | | |
|---|---|---|
| 2004/0138214 A1 | 7/2004 | Himmelsbach et al. |
| 2004/0138215 A1 | 7/2004 | Eckhardt |
| 2004/0166125 A1 | 8/2004 | Himmelsbach |
| 2005/0020574 A1 | 1/2005 | Hauel et al. |
| 2005/0026921 A1 | 2/2005 | Eckhardt |
| 2005/0130985 A1 | 6/2005 | Himmelsbach |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt |
| 2005/0234108 A1 | 10/2005 | Himmelsbach et al. |
| 2005/0261352 A1 | 11/2005 | Eckhardt |
| 2006/0004074 A1 | 1/2006 | Eckhardt |
| 2006/0058323 A1 | 3/2006 | Eckhardt et al. |
| 2006/0063787 A1 | 3/2006 | Yoshikawa |
| 2006/0079541 A1 | 4/2006 | Langkopf |
| 2006/0094722 A1 | 5/2006 | Yasuda |
| 2006/0100199 A1 | 5/2006 | Yoshikawa et al. |
| 2006/0142310 A1 | 6/2006 | Pfrengle et al. |
| 2006/0173056 A1 | 8/2006 | Kitajima |
| 2006/0205711 A1 | 9/2006 | Himmelsbach |
| 2006/0247226 A1 | 11/2006 | Himmelsbach |
| 2007/0027168 A1 | 2/2007 | Pfrengle et al. |
| 2007/0088038 A1 | 4/2007 | Eckhardt |
| 2007/0093659 A1 | 4/2007 | Bonfanti |
| 2007/0142383 A1 | 6/2007 | Eckhardt |
| 2007/0185091 A1 | 8/2007 | Himmelsbach et al. |
| 2007/0219178 A1 | 9/2007 | Muramoto |
| 2007/0259900 A1 | 11/2007 | Sieger |
| 2007/0281940 A1 | 12/2007 | Dugi |

FOREIGN PATENT DOCUMENTS

| | | |
|---|---|---|
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2590912 A1 | 6/2006 |
| DE | 10109021 A1 | 9/2002 |
| DE | 10117803 A1 | 10/2002 |
| EP | 0149578 A2 | 7/1985 |
| EP | 0400974 A2 | 5/1990 |
| EP | 0 399 285 A1 | 11/1990 |
| EP | 0 412 358 A1 | 2/1991 |
| EP | 0 524 482 A1 | 1/1993 |
| EP | 0657454 A1 | 6/1995 |
| EP | 1054012 A1 | 11/2000 |
| EP | 1338595 A2 | 8/2003 |
| EP | 1514552 A1 | 3/2005 |
| EP | 1537880 A1 | 8/2005 |
| ES | 385302 A1 | 4/1973 |
| FR | 2 707 641 A1 | 1/1995 |
| JP | S37-4895 | 6/1962 |
| JP | 2003/300977 | 10/2003 |
| JP | 2006/045156 | 2/2006 |
| WO | 91/07945 A1 | 6/1991 |
| WO | 94/03456 A1 | 2/1994 |
| WO | 99/29695 A1 | 6/1999 |
| WO | 02/02560 A2 | 1/2002 |
| WO | 02/14271 A1 | 2/2002 |
| WO | 02/24698 A1 | 3/2002 |
| WO | 02/068420 A1 | 9/2002 |
| WO | 03/004496 A1 | 1/2003 |
| WO | 03/024965 A2 | 3/2003 |
| WO | 03/057200 A2 | 7/2003 |
| WO | 03/104229 A1 | 12/2003 |
| WO | 2004/018467 A2 | 3/2004 |
| WO | 2004/018468 A2 | 3/2004 |
| WO | 2004/028524 A1 | 4/2004 |
| WO | 2004/033455 A2 | 4/2004 |
| WO | 2004/041820 A1 | 5/2004 |
| WO | 2004/046148 A1 | 6/2004 |
| WO | 2004/048379 A1 | 6/2004 |
| WO | WO 2004/050658 A1 | 6/2004 |
| WO | 2004/096806 A1 | 11/2004 |
| WO | 2004/108730 A1 | 12/2004 |
| WO | 2004/111051 A1 | 12/2004 |
| WO | 2005/058901 A1 | 6/2005 |
| WO | 2005/082906 A1 | 9/2005 |
| WO | 2005/085246 A1 | 9/2005 |
| WO | 2006/029769 A1 | 3/2006 |
| WO | 2006/048427 A1 | 5/2006 |
| WO | 2006/068163 A1 | 6/2006 |
| WO | 2007/017423 A2 | 2/2007 |
| WO | 2008/017670 A1 | 2/2008 |

OTHER PUBLICATIONS

Chemical Abstract—1991:185517 for EP 0 412 358.

Chemical Abstract—1995:543545 for FR 2 707 641.

U.S. Appl. No. 11/744,701, filed May 4, 2007, Kohlrausch.

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphs: X-Ray Powder Diffraction," Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Conarello, S.L. et al; "Mice lacking dipeptidyl peptidase IV are protected against obesity and insulin resistance," www.pnas.org/cgi/content/full/100/11/6825.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol 1: Principles and Practice, pp. 975-977, 1994, John Wiley & Sons, Inc.

Zhong, Qing et al; "Glucose-dependent insulinotropic peptide stimulates proliferation and TGF-β release from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Zejc, Alfred et al; Badania Nad Piperazynowymi Pochodnymi Dwumetyloksantyn; Acta Polon. Pharm. XXXV. Nr 4, 1976, pp. 417-421.

Januvia; Patient Information; Oct. 2007.

* cited by examiner

IMIDAZOLES AND TRIAZOLES, THEIR PREPARATION, AND THEIR USE AS PHARMACEUTICAL COMPOSITIONS

Under 35 U.S.C 119(a), hereby is claimed priority of German Patent Application No. 10 2004 030 502 that was filed on Jun. 24, 2004. Under 35 U.S.C. 119(e), hereby is claimed priority of U.S. Provisional Patent Application No. 60/590,019 that was filed on Jul. 21, 2004.

The present invention relates to substituted imidazoles and triazoles of general formula

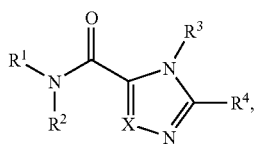

(I)

the tautomers, the stereoisomers, the mixtures thereof and the salts thereof, particularly the physiologically acceptable salts thereof with inorganic or organic acids or bases which have valuable pharmacological properties, particularly an inhibiting effect on the activity of the enzyme dipeptidylpeptidase-IV (DPP-IV), the preparation thereof, the use thereof for preventing or treating illnesses or conditions connected with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof and processes for the preparation thereof.

In European Applications EP 332 991, EP 399 285, and EP 412 358, triazoles are described as pesticides.

In the above formula I $R^1$ denotes
an aryl-$C_{1-6}$-alkyl or heteroaryl-$C_{1-6}$-alkyl group, wherein each methylene group of the alkyl group may be substituted by one or two fluorine atoms or a $C_{1-3}$-alkyl group and a methylene group may be replaced by a carbonyl group, or
an aryl-$C_{2-6}$-alkenyl or heteroaryl-$C_{2-6}$-alkenyl group, wherein the alkenyl chain may be substituted by 1 to 10 fluorine atoms or a cyano, $C_{1-3}$-alkyloxy-carbonyl, $C_{1-3}$-alkyl or nitro group, $R^2$ denotes
a hydrogen atom,
a $C_{1-6}$-alkyl group,
a $C_{1-6}$-alkyl group substituted by a group $R_a$, where
$R_a$ denotes a fluorine, chlorine or bromine atom, or a trifluoromethyl, nitro, aryl, heteroaryl, cyano, carboxy, $C_{1-4}$-alkoxy-carbonyl, amino-carbonyl, $C_{1-4}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)-piperazin-1-ylcarbonyl, $C_{1-4}$-alkylcarbonyl, arylcarbonyl, heteroarylcarbonyl, $C_{1-3}$-alkylsulphinyl or $C_{1-3}$-alkylsulphonyl group,
a $C_{2-6}$-alkyl group substituted from position 2 by a group $R_b$, where
$R_b$ denotes a hydroxy, $C_{1-3}$-alkoxy, amino, $C_{1-3}$-alkylamino, di-($C_{1-3}$-alkyl)-amino, pyrrolidin-1-yl, piperidin-1-yl, morpholin-4-yl, piperazin-1-yl or 4-($C_{1-3}$-alkyl)-piperazin-1-yl group,
an NH group substituted by a group $R_c$, where
$R_c$ denotes a $C_{1-6}$-alkyl, $C_{2-6}$-alkenyl, aryl, heteroaryl, $C_{1-4}$-alkoxycarbonyl, aminocarbonyl, $C_{1-4}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)-piperazin-1-ylcarbonyl, $C_{1-4}$-alkylcarbonyl, arylcarbonyl, heteroarylcarbonyl, $C_{1-3}$-alkylsulphinyl or $C_{1-3}$-alkylsulphonyl group,
a hydroxy group,
a $C_{1-4}$-alkoxy group, or
a $C_{2-6}$-alkenyl or $C_{2-6}$-alkynyl group, X denotes a nitrogen atom or a CH group, $R^3$ denotes
a $C_{5-7}$-cycloalkenylmethyl group optionally substituted by a $C_{1-3}$-alkyl group, an arylmethyl or heteroarylmethyl group,
a straight-chain or branched $C_{2-8}$-alkenyl group which may be substituted by 1 to 15 fluorine atoms or a cyano, nitro or $C_{1-3}$-alkoxy-carbonyl group, or
a straight-chain or branched $C_{3-6}$-alkynyl group which may be substituted by 1 to 9 fluorine atoms or a cyano, nitro or $C_{2-8}$-alkoxy-carbonyl group, and $R^4$ denotes
a pyrrolidin-1-yl or azetedin-1-yl group which is substituted in the 3 position by an amino or $C_{1-3}$-alkylamino group and may additionally be substituted by one or two $C_{1-3}$-alkyl groups,
a piperidin-1-yl or hexahydroazepin-1-yl group which is substituted in the 3 position or in the 4 position by an amino group or $C_{1-3}$-alkylamino group and may additionally be substituted by one or two $C_{1-3}$-alkyl groups,
a piperazin-1-yl or homopiperazin-1-yl group which may be substituted by one or two $C_{1-3}$-alkyl groups,
an amino group substituted by the groups $R^{15}$ and $R^{16}$ wherein
$R^{15}$ denotes a hydrogen atom, a $C_{1-6}$-alkyl, $C_{3-6}$-cycloalkyl, $C_{3-6}$-cycloalkyl-$C_{1-3}$-alkyl, aryl or aryl-$C_{1-3}$-alkyl group, and
$R^{16}$ denotes a $R^{17}$—$C_{2-3}$-alkyl group,
wherein the $C_{2-3}$-alkyl moiety is straight-chained and may be substituted by 1 to 4 $C_{1-3}$-alkyl groups, which may be identical or different, and the $C_{2-3}$-alkyl group may be linked to $R^{17}$ from position 2, and
$R^{17}$ denotes an amino or $C_{1-3}$-alkylamino group,
an amino group substituted by the groups $R^{15}$ and $R^{18}$ wherein
$R^{15}$ is as hereinbefore defined, and
$R^{18}$ denotes a $C_{3-10}$-cycloalkyl-$C_{1-2}$-alkyl- group substituted by $R^{19}$ in the 1 position of the cycloalkyl group or a $C_{3-10}$-cycloalkyl group substituted in the 1 or 2 position by a $R^{19}$—$C_{1-2}$-alkyl group, wherein $R^{19}$ denotes an amino or $C_{1-3}$-alkylamino group,
an amino group substituted by the groups $R^{15}$ and $R^{20}$ wherein
$R^{15}$ is as hereinbefore defined, and
$R^{20}$ denotes a $C_{4-10}$-cycloalkyl or $C_{4-10}$-cycloalkyl-methyl group wherein a methylene group of the $C_{4-10}$-cycloalkyl group is replaced by an —NH— group, or
an amino group substituted by the groups $R^{15}$ and $R^{21}$ wherein
$R^{15}$ is as hereinbefore defined, and
$R^{21}$ denotes a $C_{3-10}$-cycloalkyl group substituted in the 2 or 3 position by an amino or $C_{1-3}$-alkylamino group.

The above-mentioned groups $R^{18}$, $R^{20}$ and $R^{21}$ may be mono- or disubstituted by $R_d$, while the substituents may be identical or different and $R_d$ denotes a fluorine atom, a $C_{1-3}$- alkyl, trifluoromethyl, cyano, amino, $C_{1-3}$-alkylamino, hydroxy or $C_{1-3}$-alkyloxy group, and wherein one or two methylene groups of the cycloalkyl group may each be replaced independently of one another by an oxygen or sulphur atom or by an —NH— or —N($C_{1-3}$-alkyl)- group, or by a carbonyl, sulphinyl or sulphonyl group.

By the aryl groups mentioned in the definition of the above groups are meant phenyl or naphthyl groups, which may be mono-, di- or trisubstituted independently of one another by $R_h$, where the substituents may be identical or different and $R_h$ denotes a fluorine, chlorine, bromine or iodine atom, a trifluoromethyl, cyano, nitro, amino, aminocarbonyl, $C_{1-3}$-alkoxy-carbonyl, aminosulphonyl, methylsulphonyl, acetylamino, methylsulphonylamino, $C_{1-3}$-alkyl, cyclopropyl, ethenyl, ethynyl, morpholinyl, hydroxy, $C_{1-3}$-alkyloxy, difluoromethoxy or trifluoromethoxy group, and wherein additionally each hydrogen atom may be replaced by a fluorine atom.

By the heteroaryl groups mentioned in the definition of the above-mentioned groups are meant:

a pyrrolyl, furanyl, thienyl, pyridyl, indolyl, benzofuranyl, benzothiophenyl, phenanthridinyl, quinolinyl, or isoquinolinyl group, or a pyrrolyl, furanyl, thienyl or pyridyl group, wherein one or two methyne groups are replaced by nitrogen atoms, or an indolyl, benzofuranyl, benzothiophenyl, phenanthridinyl, quinolinyl, or isoquinolinyl group, wherein one to three methyne groups are replaced by nitrogen atoms, or a 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 3,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, cumarinyl, 2,3-dihydro-benzo[1,4]dioxinyl or 3,4-dihydro-3-oxo-2H-benzo[1,4]oxazinyl group, and the above-mentioned heteroaryl groups may be mono- or disubstituted by $R_h$, while the substituents may be identical or different and $R_h$ is as hereinbefore defined.

By the cycloalkyl groups mentioned in the definition of the above-mentioned groups are meant both monocyclic and polycyclic ring systems, while the polycycles may be anellated, spiro-linked, or bridged in structure. For example the term polycyclic groups denotes decalin, octahydroindene, norbornane, spiro[4,4]nonane, spiro[4,5]decane, bicyclo[2,1,1]hexane, bicyclo[2,2,2]octane, bicyclo[3,2,1]octane, bicyclo[3,2,2]nonane, bicyclo[3,3,1]nonane, bicyclo[3,3,2]decane or adamantine.

Unless otherwise stated, the above-mentioned alkyl, alkenyl and alkynyl groups may be straight-chain or branched.

The present invention includes the tautomers, enantiomers, diastereomers, the mixtures of the substituted imidazoles and triazoles of general formula I, and the prodrugs and the salts thereof.

The carboxy groups mentioned in the definition of the above-mentioned groups may be replaced by a group which can be converted in vivo into a carboxy group or by a group which is negatively charged under physiological conditions.

Moreover, the amino and imino groups mentioned in definition of the above-mentioned groups may be substituted by a group which can be cleaved in vivo. Such groups are described for example in WO 98/46576 and by N. M. Nielsen et al. in International Journal of Pharmaceutics 39, 75-85 (1987).

By a group which can be converted in vivo into a carboxy group is meant, for example, a hydroxymethyl group, a carboxy group esterified with an alcohol wherein the alcohol moiety is preferably a $C_{1-6}$-alkanol, a phenyl-$C_{1-3}$-alkanol, a $C_{3-9}$-cycloalkanol, while a $C_{5-8}$-cycloalkanol may additionally be substituted by one or two $C_{1-3}$-alkyl groups, a $C_{5-8}$-cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkoxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol with the proviso that no bonds to the oxygen atom start from a carbon atom which carries a double or triple bond, a $C_{3-8}$-cycloalkyl-$C_{1-3}$-alkanol, a bicycloalkanol with a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of formula

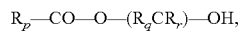

wherein $R_p$ denotes a $C_{1-8}$-alkyl, $C_{5-7}$-cycloalkyl, $C_{1-8}$-alkyloxy, $C_{5-7}$-cycloalkyloxy, phenyl or phenyl-$C_{1-3}$-alkyl group, $R_q$ denotes a hydrogen atom, a $C_{1-3}$-alkyl, $C_{5-7}$-cycloalkyl or phenyl group, and $R_r$ denotes a hydrogen atom or a $C_{1-3}$-alkyl group.

By a group which is negatively charged under physiological conditions is meant, for example, a tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group and by a group which can be cleaved in vivo from an imino or amino group is meant, for example, a hydroxy group, an acyl group, such as a phenylcarbonyl group, optionally mono- or disubstituted by fluorine, chlorine, bromine, or iodine atoms, by $C_{1-3}$-alkyl or $C_{1-3}$-alkoxy groups, while the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-16}$-alkoxycarbonyl or $C_{1-16}$-alkylcarbonyloxy group, wherein hydrogen atoms may be wholly or partially replaced by fluorine or chlorine atoms such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkoxycarbonyl group such as the benzyloxycarbonyl, phenylethoxycarbonyl or phenylpropoxycarbonyl group, a 3-amino-propionyl group wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl, $R_p$—CO—O—$(R_qCR_r)$—O—CO, $C_{1-6}$-alkyl-CO—NH—$(R_sCR_t)$—O—CO— or $C_{1-6}$-alkyl-CO—O—$(R_sCR_t)$—$(R_sCR_t)$—O—CO— group, wherein $R_p$ to $R_r$ are as hereinbefore defined, and $R_s$ and $R_t$, which may be identical or different, denote hydrogen atoms or $C_{1-3}$-alkyl groups.

Moreover, unless otherwise stated, the saturated alkyl and alkoxy moieties containing more than 2 carbon atoms mentioned in the definitions above also include the branched isomers thereof such as the isopropyl, tert.butyl, isobutyl group, etc.

$R^1$ may denote, for example, a 2-cyanobenzyl, 3-fluorobenzyl, 3-methoxybenzyl, 4-bromo-2-cyanobenzyl, 3-chloro-2-cyanobenzyl, 2-cyano-4-fluorobenzyl, 3,5-dimethoxybenzyl, 2,6-dicyanobenzyl, 5-cyanofuranylmethyl, oxazolylmethyl, isoxazolylmethyl, 5-methoxycarbonylthienylmethyl, pyridinylmethyl, 3-cyanopyridin-2-ylmethyl, 6-cyanopyridin-2-ylmethyl, 6-fluoropyridin-2-ylmethyl, pyrimidin-2-ylmethyl, 4-methyl-pyrimidin-2-ylmethyl, 4,6-dimethyl-pyrimidin-2-ylmethyl, 3-(2-cyanophenyl)-prop-2-enyl, 3-(pyridin-2-yl)-prop-2-enyl, 3-(pentafluorophenyl)-prop-2-enyl, phenyl-carbonylmethyl, 3-methoxyphenylcarbonylmethyl, naphth-1-ylmethyl, 4-cyanonaphth-1-ylmethyl, quinolin-1-ylmethyl, 4-cyanoquinolin-1-ylmethyl, isoquinolin-1-ylmethyl, 4-cyanoisoquinolin-1-ylmethyl, 3-methylisoquinolin-1-ylmethyl, quinazolin-2-ylmethyl, 4-methylquinazolin-2-ylmethyl, [1,5]naphthiridin-2-ylmethyl, [1,5]naphthiridin-3-ylmethyl, phenanthridin-6-ylmethyl, quinoxalin-6-ylmethyl or 2,3-dimethyl-quinoxalin-6-ylmethyl group.

$R^2$ may denote, for example, a hydrogen atom, a methyl, ethyl, propyl, butyl, 2-propen-1-yl, 2-propyn-1-yl, benzyl, 2-phenylethyl, phenylcarbonylmethyl, 3-phenylpropyl, hydroxy, 2-hydroxyethyl, 2-methoxyethyl, 2-ethoxyethyl, 2-(dimethylamino)ethyl, 2-(diethylamino)ethyl, 3-hydroxypropyl, 3-methoxypropyl, 3-(dimethylamino)propyl, 3-(pyrrolidino)propyl, 3-(piperidino)propyl, 3-(morpholino)propyl, 3-(piperazino)propyl, 3-(4-methylpiperazino)propyl, carboxymethyl, (methoxycarbonyl)methyl, (ethoxycarbonyl)methyl, 2-carboxyethyl, 2-(methoxycarbonyl)ethyl, 2-(ethoxycarbonyl)ethyl, 3-carboxypropyl, 3-(methoxycarbonyl)propyl, 3-(ethoxycarbonyl)propyl, (aminocarbonyl)methyl, (methylaminocarbonyl)methyl, (dimethylaminocarbonyl)methyl, (pyrrolidinocarbonyl)methyl, (piperidinocarbonyl)methyl, (morpholinocarbonyl)methyl, 2-(aminocarbonyl)ethyl, 2-(methylaminocarbonyl)ethyl, 2-(dimethylaminocarbonyl)-ethyl, 2-(pyrrolid inocarbonyl)ethyl, 2-(piperidinocarbonyl)ethyl, 2-(morpholinocarbonyl)ethyl, phenylcarbonylmethyl, cyanomethyl, 2-cyanoethyl, pyridin-3-ylmethyl, pyridin-4-ylmethyl, methylamino, ethylamino, methoxycarbonylamino, ethoxycarbonylamino, methylcarbonylamino, ethylcarbonylamino, aminocarbonylamino, methylaminocarbonylamino, dimethylaminocarbonylamino, methylsulphonylamino, phenylamino or pyridin-2-ylamino group.

$R^3$ may denote, for example, a 2-propen-1-yl, 2-methyl-2-propen-1-yl, 1-buten-1-yl, 2-buten-1-yl, 3-buten-1-yl, 2-methyl-2-buten-1-yl, 3-methyl-2-buten-1-yl, 2,3-dimethyl-2-buten-1-yl, 3-methyl-3-buten-1-yl, 1-cyclopenten-1-ylmethyl, (2-methyl-1-cyclopenten-1-yl)methyl, 1-cyclohexen-1-ylmethyl, 2-propyn-1-yl, 2-butyn-1-yl, 3-butyn-1-yl, 2-chlorobenzyl, 2-bromobenzyl, 2-Iodbenzyl, 2-cyanobenzyl, 3-fluorobenzyl, 2-methoxybenzyl, 2-furanylmethyl, 3-furanylmethyl, 2-thienylmethyl or 3-thienylmethyl group.

$R^4$ may denote, for example, a 3-aminopyrrolidin-1-yl, 3-aminopiperidin-1-yl, 3-(methylamino)-piperidin-1-yl, 3-(ethylamino)-piperidin-1-yl, 3-amino-2-methyl-piperidin-1-yl, 3-amino-3-methyl-piperidin-1-yl, 3-amino-4-methyl-piperidin-1-yl, 3-amino-5-methyl-piperidin-1-yl, 3-amino-6-methyl-piperidin-1-yl, 4-aminopiperidin-1-yl, 3-amino-hexahydroazepin-1-yl, 4-amino-hexahydroazepin-1-yl, (2-aminocyclopropyl)amino, (2-aminocyclobutyl)amino, (3-aminocyclobutyl)amino, (2-aminocyclopentyl)amino, (3-aminocyclopentyl)amino, (2-aminocyclohexyl)amino, (3-aminocyclohexyl)amino, piperazin-1-yl, homopiperazin-1-yl, N-(2-aminoethyl)-N-methylamino, N-(2-aminopropyl)-N-methylamino or N-(2-amino-2-methyl-propyl)-N-methylamino group.

Preferred compounds of the above general formula I are those wherein
$R^1$ and $R^2$ are as hereinbefore defined,
X denotes a nitrogen atom or a CH group,
$R^3$ denotes a 1-buten-1-yl, 2-buten-1-yl, 3-methyl-2-buten-1-yl, 2-butyn-1-yl, cyclopent-1-enyl-methyl, furanylmethyl, thienylmethyl, chlorobenzyl, bromobenzyl, iodobenzyl, methoxybenzyl or cyanobenzyl group, and
$R^4$ denotes
an N-(2-aminoethyl)-N-methyl-amino group which may be substituted in the ethyl moiety by one or two $C_{1-3}$-alkyl groups, or
a 3-aminopiperidin-1-yl, piperazin-1-yl or [1,4]diazepan-1-yl group, while the above-mentioned groups may each additionally be substituted by one or two $C_{1-3}$-alkyl groups, the enantiomers, the diastereomers, the mixtures thereof and the salts thereof.

Particularly preferred compounds of the above general formula I are those wherein:
$R^1$ denotes a phenylmethyl, phenylcarbonylmethyl, phenylprop-2-enyl, pyridinylmethyl, pyrimidinylmethyl, naphthylmethyl, quinolinylmethyl, isoquinolinylmethyl, quinazolinylmethyl, quinoxalinylmethyl, phenanthridinylmethyl, naphthyridinylmethyl or benzotriazolylmethyl group, while all the above-mentioned aryl and heteroaryl groups may be substituted by one or two fluorine, chlorine or bromine atoms or one or two cyano, nitro, amino, $C_{1-3}$-alkyl, $C_{1-3}$-alkyloxy or morpholinyl groups, while the substituents are identical or different,
$R^2$ denotes a hydrogen atom or a methyl group,
X denotes a nitrogen atom or a CH group,
$R^3$ denotes a 1-buten-1-yl, 2-buten-1-yl, 3-methyl-2-buten-1-yl, 2-butyn-1-yl, cyclopent-1-enyl-methyl, furanylmethyl, thienylmethyl, benzyl, chlorobenzyl, bromobenzyl, iodobenzyl or cyanobenzyl group and
$R^4$ denotes an N-(2-aminoethyl)-N-methylamino, N-(2-aminopropyl)-N-methylamino, 3-aminopiperidin-1-yl, piperazin-1-yl or [1,4]diazepan-1-yl group,
the enantiomers, the diastereomers, the mixtures thereof and the salts thereof.

Most particularly preferred compounds of the above general formula I are those wherein
$R^1$ denotes a phenylethyl, naphthylmethyl, methylisoquinolinylmethyl, quinolinylmethyl or phenanthridinylmethyl group,
$R^2$ denotes a hydrogen atom or a methyl group,
X denotes a nitrogen atom or a CH group, $R^3$ denotes a 3-methyl-2-buten-1-yl, 2-butyn-1-yl, benzyl or 2-chlorobenzyl group and $R^4$ denotes a 3-aminopiperidin-1-yl, [1,4]diazepan-1-yl or piperazin-1-yl group, the enantiomers, the diastereomers, the mixtures and salts thereof.

Particularly preferred compounds of general formula I are those wherein $R^1$ to $R^3$ and X are as hereinbefore defined and $R^4$ denotes a 3-aminopiperidin-1-yl group, the tautomers, the enantiomers, the diastereomers, the mixtures and salts thereof.

The following preferred compounds are mentioned by way of example:

(1) 1-(but-2-ynyl)-2-(3-amino-piperidin-1-yl)-5-(naphth-1-ylmethylaminocarbonyl)-1H-imidazole (2) 1-(but-2-ynyl)-2-(3-amino-piperidin-1-yl)-5-[N-(naphth-1-ylmethyl)-N-methylaminocarbonyl]-1H-imidazole (3) 1-(but-2-ynyl)-2-(3-amino-piperidin-1-yl)-5-(phenanthridin-6-ylmethylaminocarbonyl)-1H-imidazole (4) 1-(but-2-ynyl)-2-(3-amino-piperidin-1-yl)-5-(3-methyl-isoquinolin-1-ylmethylaminocarbonyl)-1H-imidazole (5) 1-(but-2-ynyl)-2-(3-amino-piperidin-1-yl)-5-(quinolin-3-ylmethylaminocarbonyl)-1H-imidazole (6) 1-(but-2-ynyl)-2-(3-amino-piperidin-1-yl)-5-(2-phenyl-ethylaminocarbonyl)-1H-imidazole (7) 3-(piperazin-1-yl)-4-(3-methyl-but-2-enyl)-5-(naphth-1-ylmethylaminocarbonyl)-4H-[1,2,4]triazole (8) 3-(piperazin-1-yl)-4-benzyl-5-(naphth-1-ylmethylaminocarbonyl)-4H-[1,2,4]triazole (9) 3-([1,4]diazepan-1-yl)-4-(3-methyl-but-2-enyl)-5-(naphth-1-ylmethylaminocarbonyl)-4H-[1,2,4]triazole

(10) 3-(3-amino-piperidin-1-yl)-4-(3-methyl-but-2-enyl)-5-(naphth-1-ylmethylaminocarbonyl)-4H-[1,2,4]triazole

(11) 3-(3-amino-piperidin-1-yl)-4-benzyl-5-(naphth-1-ylmethylaminocarbonyl)-4H-[1,2,4]triazole

(12) 3-(3-amino-piperidin-1-yl)-4-(2-chloro-benzyl)-5-(naphth-1-ylmethylaminocarbonyl)-4H-[1,2,4]triazole

(13) 3-(3-amino-piperidin-1-yl)-4-(but-2-ynyl)-5-(3-methyl-isoquinolin-1-ylmethylaminocarbonyl)-4H-[1,2,4]triazole

(14) 3-(3-amino-piperidin-1-yl)-4-(but-2-ynyl)-5-(quinolin-6-ylmethylaminocarbonyl)-4H-[1,2,4]triazole

(15) 3-(3-amino-piperidin-1-yl)-4-(but-2-ynyl)-5-(phenanthridin-6-ylmethylaminocarbonyl)-4H-[1,2,4]triazole and the salts thereof.

A preferred sub-group comprises the compounds of general formula I as hereinbefore defined wherein X denotes a nitrogen atom.

A second preferred sub-group comprises the compounds of general formula I as hereinbefore defined, wherein X denotes a CH group.

According to the invention the compounds of general formula I are obtained by methods known, per se, for example by the following methods:

a) in order to prepare a compound of general formula I wherein X is a nitrogen atom: reacting a compound of general formula

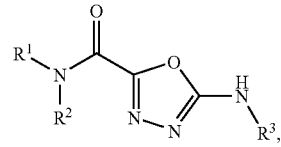

(II)

wherein $R^1$ to $R^3$ are as hereinbefore defined, with a compound of general formula

H—$R^4$ (III), wherein $R^4$ is as hereinbefore defined.

The reaction is expediently carried out in a high-boiling solvent such as butanol, mesitylene, chlorobenzene, dimethylsulphoxide, ethylenglycol diethyl ether or sulpholane, optionally in the presence of an inorganic or organic base, such as e.g. sodium carbonate or potassium hydroxide or N-ethyl-diisopropylamine (Hünig base), while these organic bases may simultaneously also serve as solvent, at temperatures between 80 and 200° C. The reaction is preferably carried out without a solvent in an excess of the compound of general formula III used, at 150-200° C., while heating in a microwave oven is preferably to heating by conventional methods.

b) in order to prepare a compound of general formula I wherein X is a CH group: diazotisation followed by reduction of a compound of general formula

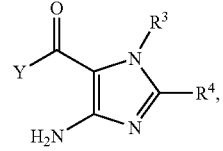

(IV)

wherein Y denotes a substituted oxygen or nitrogen atom, for example a $C_{1-6}$-alkoxy, di-($C_{1-4}$-alkyl)-amino, or —$NR^1R^2$ group, wherein $R^1$ is as hereinbefore defined and $R^2$ is as hereinbefore defined, with the exception of the hydrogen atoms, and $R^3$ and $R^4$ are as hereinbefore defined, and optionally converting the group Y into the group —$NR^1R^2$, wherein $R^1$ and $R^2$ are as hereinbefore defined.

The diazotisation is carried out with inorganic or organic nitrites, such as, e.g., sodium nitrite or isoamyl nitrite, in the presence of an acid, such as e.g. hydrochloric acid, sulphuric acid, acetic acid, or boron trifluoride etherate, in a solvent such as water, alcohol, ether, tetrahydrofuran, acetonitrile, dimethylformamide or dichloromethane. The reaction is conveniently carried out at temperatures from −10° C. to 30° C. The diazo compound formed may be isolated as a salt, such as, e.g., tetrafluoroborate, or better still is further reacted directly with the reducing agent. Suitable reducing agents include for example hydrides, such as sodium cyanoborohydride, hypophosphites, sulphites, iron, iron (II) salts or copper (I) salts. The reduction is preferably carried out between −10° C. and 100° C.

c) In order to prepare a compound of general formula I, wherein $R^4$ according to the definition provided hereinbefore contains an amino group or an alkylamino group optionally substituted in the alkyl moiety:

deprotecting a compound of general formula

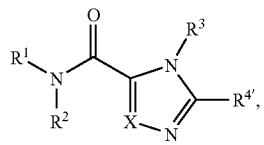

wherein $R^1$, $R^2$, X and $R^3$ are as hereinbefore defined and $R^{4'}$ contains a N-tert.-butyloxycarbonylamino, N-tert.-butyloxycarbonyl-N-alkylamino, phthalimido or azido group, while the alkyl moiety of the N-tert.-butyloxycarbonyl-N-alkylamino group may be substituted as mentioned hereinbefore.

A tert.-butyloxycarbonyl group is preferably cleaved by treating with an acid such as trifluoroacetic acid or hydrochloric acid or by treating with bromotrimethylsilane or iodotrimethylsilane, optionally using a solvent such as methylene chloride, ethyl acetate, dioxane, methanol, isopropanol or diethyl ether at temperatures between 0 and 80° C.

A phthalyl group is preferably cleaved in the presence of ethanolamine, hydrazine or a primary amine such as methylamine, ethylamine or n-butylamine, in a solvent such as methanol, ethanol, isopropanol, toluene, water or dioxane at temperatures between 20 and 100° C.

The reduction of an azide group to form the corresponding amine is preferably carried out in the presence of a phosphine such as triphenyl, trimethyl, triethyl or tributylphosphine in a solvent such as tetrahydrofuran, dioxane or toluene at temperatures between 0 and 110° C. Alternatively the reduction may also be carried out with hydrogen in the presence of a transition metal catalyst such as e.g. palladium on charcoal in ethyl acetate, alcohol, ether, acetic acid, or water at temperatures between 0 and 80° C.

If, according to the invention, a compound of general formula I is obtained that contains an amino, alkylamino, or imino group, this may be converted by acylation or sulphonylation into a corresponding acyl or sulphonyl compound of general formula I.

If a compound of general formula I is obtained which contains an amino, alkylamino or imino group, this may be converted by alkylation or reductive alkylation into a corresponding alkyl compound of general formula I.

If a compound of general formula I is obtained which contains a carboxy group, this may be converted by esterification into a corresponding ester of general formula I.

If a compound of general formula I is obtained which contains a carboxy or ester group, this may be converted by reaction with an amine into a corresponding amide of general formula I.

The subsequent esterification is optionally carried out in a solvent or mixture of solvents such as methylene chloride, dimethylformamide, benzene, toluene, chlorobenzene, tetrahydrofuran, benzene/tetrahydrofuran or dioxane or particularly advantageously in a corresponding alcohol, optionally in the presence of an acid such as hydrochloric acid or in the presence of a dehydrating agent, e.g. in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole and optionally additionally in the presence of 4-dimethylamino-pyridine, N,N'-carbonyldiimidazole or triphenylphosphine/carbon tetrachloride, conveniently at temperatures between 0 and 150° C., preferably at temperatures between 0 and 80° C.

The subsequent ester formation may also be carried out by reacting a compound which contains a carboxy group with a corresponding alkyl halide.

The subsequent acylation or sulphonylation is optionally carried out in a solvent or mixture of solvents such as methylene chloride, dimethylformamide, benzene, toluene, chlorobenzene, tetrahydrofuran, benzene/tetrahydrofuran or dioxane with a corresponding acyl or sulphonyl derivative, optionally in the presence of a tertiary organic base or in the presence of an inorganic base or in the presence of a dehydrating agent, e.g. in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole and optionally additionally in the presence of 4-dimethylamino-pyridine, N,N'-carbonyldiimidazole or triphenylphosphine/carbon tetrachloride, conveniently at temperatures between 0 and 150° C., preferably at temperatures between 0 and 80° C.

The subsequent alkylation is optionally carried out in a solvent or mixture of solvents such as methylene chloride, dimethylformamide, benzene, toluene, chlorobenzene, tetrahydrofuran, benzene/tetrahydrofuran or dioxane with an alkylating agent such as a corresponding halide or sulphonic acid ester, e.g. with methyl iodide, ethyl bromide, dimethylsulphate or benzyl chloride, optionally in the presence of a tertiary organic base or in the presence of an inorganic base, conveniently at temperatures between 0 and 150° C., preferably at temperatures between 0 and 100° C.

The subsequent reductive alkylation is carried out with a corresponding carbonyl compound such as formaldehyde, acetaldehyde, propionaldehyde, acetone or butyraldehyde in the presence of a complex metal hydride such as sodium borohydride, lithium borohydride, sodium triacetoxyborohydride or sodium cyanoborohydride, conveniently at a pH of 6-7 and at ambient temperature or in the presence of a hydrogenation catalyst, e.g., with hydrogen in the presence of palladium/charcoal, under a hydrogen pressure of 1 to 5 bar. The methylation may also be carried out in the presence of formic acid as reducing agent at elevated temperatures, e.g. at temperatures between 60 and 120° C.

The subsequent amide formation is carried out by reacting a corresponding reactive carboxylic acid derivative with a corresponding amine, optionally in a solvent or mixture of solvents such as methylene chloride, dimethylformamide, benzene, toluene, chlorobenzene, tetrahydrofuran, benzene/tetrahydrofuran or dioxane, while the amine used may simultaneously serve as solvent, optionally in the presence of a tertiary organic base or in the presence of an inorganic base or with a corresponding carboxylic acid in the presence of a dehydrating agent, e.g. in the presence of isobutyl chloroformate, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide or 1-hydroxy-benzotriazole and optionally additionally in the presence of 4-dimethylamino-pyridine, N,N'-carbonyldiimidazole or triphenylphosphine/carbon tetrachloride, conveniently at temperatures between 0 and 150° C., preferably at temperatures between 0 and 80° C.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, acetyl, benzoyl, methyl, ethyl, tert-butyl, trityl, benzyl or tetrahydropyranyl group, Protecting groups for a carboxy group may be a trimethylsilyl, methyl, ethyl, tert.butyl, benzyl, or tetrahydropyranyl group.

Protecting groups for an amino, alkylamino or imino group may be a formyl, acetyl, trifluoroacetyl, ethoxycarbonyl, tert-butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g., in water, isopropanol/water, acetic acid/water, tetrahydrofuran/water or dioxan/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl, or benzyloxycarbonyl group is cleaved, for example, hydrogenolytically, i.e., with hydrogen in the presence of a catalyst such as palladium/charcoal in a suitable solvent such as methanol, ethanol, ethyl acetate, or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably from 3 to 5 bar. However, a 2,4-dimethoxybenzyl group is preferably cleaved in trifluoroacetic acid in the presence of anisole.

A tert.-butyl or tert.-butyloxycarbonyl group is preferably cleaved by treating with an acid such as trifluoroacetic acid or hydrochloric acid or by treating with iodotrimethylsilane, optionally using a solvent such as methylene chloride, dioxan, methanol or diethyl ether.

A trifluoroacetyl group is preferably cleaved by treating with an acid such as hydrochloric acid optionally in the presence of a solvent such as acetic acid at temperatures between 50 and 120° C. or by treating with sodium hydroxide solution optionally in the presence of a solvent such as tetrahydrofuran at temperatures between 0 and 50° C.

A phthalyl group is preferably cleaved in the presence of hydrazine or a primary amine such as methylamine, ethylamine, or n-butylamine in a solvent such as methanol, ethanol, isopropanol, toluene/water or dioxan at temperatures between 20 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be separated by chromatography into their cis and trans isomers, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+)- or (−)-menthol and an optically active acyl group in amides, for example, may be a (+)- or (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the new compounds of formula (I), if they contain a carboxy group, may if desired be converted into the salts thereof with inorganic or organic bases, particularly for pharmaceutical use into the physiologically acceptable salts thereof. Suitable bases for this include, for example, sodium hydroxide, potassium hydroxide, cyclohexylamine, ethanolamine, diethanolamine, and triethanolamine.

The compounds of general formulae II and IV used as starting compounds are either known from the literature or may be prepared by methods known from the literature (see Examples I to XII).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in an experiment in which an extract of the human colon carcinoma cell line Caco-2 is used as the DPP IV source. The differentiation of the cells in order to induce the DPP-IV expression was carried out in accordance with the description by Reiher et al. in an article entitled "Increased expression of intestinal cell line Caco-2", which appeared in Proc. Natl. Acad. Sci. Vol. 90, pp. 5757-5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifugation at 35,000 g for 30 minutes at 4° C. (to remove cell debris).

The DPP-IV assay was carried out as follows:

50 µl of substrate solution (AFC; AFC is amido-4-trifluoromethylcoumarin), final concentration 100 µM, were placed in black microtitre plates. 20 µl of assay buffer (final concentrations 50 mM Tris HCl pH 7.8, 50 mM NaCl, 1% DMSO) was pipetted in. The reaction was started by the addition of 30 µl of solubilised Caco-2 protein (final concentration 0.14 µg of protein per well). The test substances under investigation were typically added prediluted to 20 µl, while the volume of assay buffer was then reduced accordingly. The reaction was carried out at ambient temperature, the incubation period was 60 minutes. Then the fluorescence was measured in a Victor 1420 Multilabel Counter, with the excitation wavelength at 405 nm and the emission wavelength at 535 nm. Dummy values (corresponding to 0% activity) were obtained in mixtures with no Caco-2 protein (volume replaced by assay buffer), control values (corresponding to 100% activity) were obtained in mixtures without any added substance. The potency of each test substance in question, expressed as $IC_{50}$ values, was calculated from dosage/activity curves consisting of 11 measured points in each case. The following results were obtained:

| Compound (Example no.) | DPP IV inhibition $IC_{50}$ [nM] |
|---|---|
| 1 | 106 |
| 1(2) | 41 |
| 1(3) | 99 |
| 2 | 367 |
| 2(2) | 386 |
| 3 | 101 |
| 3(1) | 101 |
| 4 | 382 |
| 4(1) | 24 |
| 4(2) | 36 |

The compounds prepared according to the invention are well tolerated as no changes in the behavior of rats could be detected in the animals after the oral administration of 10 mg/kg of the compound of Example 4(1), for example.

In view of their ability to inhibit DPP-IV activity, the compounds of general formula I according to the invention and the corresponding pharmaceutically acceptable salts thereof are suitable for influencing any conditions or diseases which can be affected by the inhibition of the DDP-IV activity. It is therefore to be expected that the compounds according to the invention will be suitable for the prevention or treatment of diseases or conditions such as type 1 and type 2 diabetes mellitus, diabetic complications (e.g., retinopathy, nephropathy or neuropathies), metabolic acidosis or ketosis, reactive hypoglycaemia, insulin resistance, metabolic syndrome, dyslipidaemias of various origins, arthritis, atherosclerosis and related diseases, obesity, allograft transplantation and osteoporosis caused by calcitonin. In addition, these substances are suitable for preventing B-cell degeneration such as e.g. apoptosis or necrosis of pancreatic B-cells. The substances are also suitable for improving or restoring the function of pancreatic cells and additionally increasing the size and number of pancreatic B-cells. Additionally, on the basis of the role of the glucagon-like peptides such as, e.g., GLP-1 and GLP-2 and their link with DPP-IV inhibition, it is expected that the compounds according to the invention will be suitable for achieving, inter alia, a sedative or tranquillising effect, as well as having a favourable effect on catabolic states after operations or hormonal stress responses or possibly reducing mortality and morbidity after myocardial infarct. Moreover, they are suitable for treating any conditions connected with the effects mentioned above and mediated by GLP-1 or GLP-2. The compounds according to the invention may also be used as diuretics or antihypertensives and are suitable for preventing and treating acute kidney failure. The compounds according to the invention may also be used to treat inflammatory complaints of the respiratory tract. They are also suitable for preventing and treating chronic inflammatory bowel diseases such as, e.g., irritable bowel syndrome (IBS), Crohn's disease or ulcerative colitis and also pancreatitis. It is also expected that they can be used for all kinds of injury or damage to the gastrointestinal tract such as may occur in colitis and enteritis, for example. Moreover, it is expected that DPP-IV inhibitors and hence the compounds according to the invention can be used to treat infertility or to improve fertility in humans or mammals, particularly if the infertility is connected with insulin resistance or with polycystic ovary syndrome. On the other hand these substances are suitable for influencing sperm motility and are thus suitable for use as male contraceptives. In addition, the substances are suitable for treating growth hormone deficiencies connected with restricted growth, and may reasonably be used for all indications for which growth hormone may be used. The compounds according to the invention are also suitable, on the basis of their inhibitory effect on DPP-IV, for treating various autoimmune diseases such as, e.g., rheumatoid arthritis, multiple sclerosis, thyroiditis and Basedow's disease, etc. They may also be used to treat viral diseases and also, for example, in HIV infections, for stimulating blood production, in benign prostatic hyperplasia, gingivitis, as well as for the treatment of neuronal defects and neurodegenerative diseases such as Alzheimer's disease, for example. The compounds described may also be used for the treatment of tumors, particularly for modifying tumor invasion and also metastasisation; examples here are their use in treating T-cell lymphomas, acute lymphoblastic leukaemia, cell-based thyroid carcinomas, basal cell carcinomas or breast cancers. Other indications are stroke, ischaemia of various origins, Parkinson's disease and migraine. In addition, further indications include follicular and epidermal hyperkeratoses, increased keratinocyte proliferation, psoriasis, encephalomyelitis, glomerulonephritis, lipodystrophies, as well as psychosomatic, depressive, and neuropsychiatric diseases of all kinds.

The compounds according to the invention may also be used in conjunction with other active substances. Suitable therapeutic agents for such combinations include for example antidiabetic agents such as metformin, sulphonylureas (e.g. glibenclamide, tolbutamide, glimepiride), nateglinide, repaglinide, thiazolidinediones (e.g. rosiglitazone, pioglitazone), PPAR-gamma agonists (e.g. GI 262570) and antagonists, PPAR-gamma/alpha modulators (e.g. KRP 297), alpha-glucosidase inhibitors (e.g. acarbose, voglibose), other DPPIV inhibitors, alpha2 antagonists, insulin and insulin analogues, GLP-1 and GLP-1 analogues (e.g. exendin-4) or amylin. Also, combinations with SGLT2 inhibitors, such as T-1095 or KGT-1251 (869682), inhibitors of protein tyrosine phosphatase 1, substances which influence deregulated glucose production in the liver, such as, e.g., inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g., simvastatin, atorvastatin), fibrates (e.g. bezafibrate, fenofibrate), nicotinic acid and its derivatives, PPAR-alpha agonists, PPAR-delta agonists, ACAT inhibitors (e.g., avasimibe) or cholesterol absorption inhibitors such as for example ezetimibe, bile acid-binding substances such as for example cholestyramine, inhibitors of ileac bile acid transport, HDL-raising compounds such as for example inhibitors of CETP or regulators of ABC1 or active substances for the treatment of obesity, such as e.g. sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or $\beta_3$-agonists such as SB418790 or AD-9677 as well as agonists of the 5HT2c receptor.

It is also possible to combine the compounds with drugs for treating high blood pressure, such as, e.g., AII antagonists or ACE inhibitors, diuretics, β-blockers, Ca-antagonists, etc., or combinations thereof.

The dosage required to expediently achieve such an effect is, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

Preparation of the starting compounds:

EXAMPLE I 1-ethoxycarbonylmethyl-3-cyano-2-phenyl-isourea 29.3 g glycine ethylester hydrochloride are added to a solution of 50.0 g diphenyl-N-cyano-carbonimidate in 29 ml triethylamine and 500 ml isopropanol. The solution is stirred for 16 h (hours) at ambient temperature and then evaporated down. The residue is dissolved in ethyl acetate and the organic phase is washed with water and aqueous potassium carbonate solution. The organic phase is dried over sodium sulphate and the solvent is eliminated completely. The residue is washed with diethyl ether and dried.

Yield: 35.5 g (68% of theory)
Mass spectrum (ESI$^+$): m/z=248 [M+H]$^+$

EXAMPLE II 1-ethoxycarbonylmethyl-1-(but-2-ynyl)-3-cyano-2-phenyl-isourea 11 ml but-2-ynylbromide are added to a mixture of 30.2 g 1-ethoxycarbonylmethyl-3-cyano-2-phenyl-isourea and 20.0 g potassium carbonate in 200 ml acetone. After 1 d (day) stirring at ambient temperature a further 6.5 g potassium carbonate and 3.5 ml but-2-ynylbromide are added. After another 20 h at ambient temperature the solvent is removed and ethyl acetate is added. The organic phase is washed with water, dried over sodium sulphate and evaporated to dryness.

Yield: 35.2 g (96% of theory)
Mass spectrum (ESI$^+$): m/z=300 [M+H]$^+$

EXAMPLE III 3-tert-butoxycarbonylamino-N-(ethoxycarbonylmethyl)-N-(but-2-ynyl)-N'-cyano-piperidin-1-carboxamidine 10.0 g 1-ethoxycarbonylmethyl-1-(but-2-ynyl)-3-cyano-2-phenyl-isourea are added to a mixture of 10.0 g 3-tert-butoxycarbonylaminopiperidine and 4.8 g potassium carbonate in 50 ml of dimethylformamide. The reaction mixture is stirred for 1 d at ambient temperature and then a further 1.6 g potassium carbonate and 3.0 g 3-tert-butoxycarbonylaminopiperidine are added. After another 3 d at ambient temperature water is added and the mixture is extracted with ethyl acetate. The organic extracts are dried over sodium sulphate, the solvent is removed, and the residue is purified on silica gel (cyclohexane/ethyl acetate 5:1->1:2).

Yield: 12.5 g (approx. 90%, 83% of theory)
Mass spectrum (ESI$^+$): m/z=406 [M+H]$^+$

EXAMPLE IV

Ethyl 5-amino-2-(3-tert-butoxycarbonylamino-piperidin-1-yl)-3-(but-2-ynyl)-3H-imidazole-4-carboxylate 2.5 g sodium ethoxide are added to a solution of 12.5 g (approx. 90%) 3-tert-butoxycarbonylamino-N-(ethoxycarbonylmethyl)-N-(but-2-ynyl)-N'-cyano-piperidine-1-carboxamidine in 100 ml dry ethanol. The reaction solution is stirred for 3 h at ambient temperature and then neutralised with 1 M hydrochloric acid. The solvent is removed, water is added and the mixture is extracted with ethyl acetate. The organic extracts are dried over sodium sulphate, the solvent is removed, and the residue is purified on silica (cyclohexane/ethyl acetate 3:1->1:5).

Yield: 5.7 g (51% of theory)
Mass spectrum (ESI$^+$): m/z=406 [M+H]$^+$

EXAMPLE V

Ethyl 2-(3-tert-butoxycarbonylamino-piperidin-1-yl)-3-(but-2-ynyl)-3H-imidazole-4-carboxylate A solution of 3.00 g ethyl 5-amino-2-(3-tert-butoxycarbonylamino-piperidin-1-yl)-3-(but-2-ynyl)-3H-imidazole-4-carboxylate in 36 ml 2 M hydrochloric acid is cooled to 0° C. To this is added a solution of 0.60 g sodium nitrite in 2 ml of water and the reaction mixture is stirred for 1 h at 0° C. Then 8.4 ml hypophosphorous acid are added and the mixture is stirred for a further 14 h at 0° C. Then the reaction mixture is added to ice-cooled aqueous potassium carbonate solution and extracted with dichloromethane. The organic extracts are dried over sodium sulphate and evaporated down. The residue is dissolved in 8 ml dichloromethane, and 1.62 g di-tert-butyl carbonate are added. The solution is stirred for 2 h at ambient temperature, then evaporated to dryness and chromatographed on silica gel (cyclohexane/ethyl acetate 7:3->1:1).

Yield: 1.62 g (56% of theory)
Mass spectrum (ESI$^+$): m/z=391 [M+H]$^+$

EXAMPLE VI 2-(3-tert-butoxycarbonylamino-piperidin-1-yl)-3-(but-2-ynyl)-3H-imidazole-4-carboxylic acid A solution of 4.40 g ethyl 2-(3-tert-butoxycarbonylamino-piperidin-1-yl)-3-(but-2-ynyl)-3H-imidazole-4-carboxylate in 28 ml 4 M potassium hydroxide solution and 20 ml of tetrahydrofuran is stirred for 14 h at 100° C. Then the solution is neutralized with 2 M hydrochloric acid and extracted with dichloromethane. The combined organic extracts are dried over sodium sulphate and evaporated to dryness.

Yield: 3.12 g (76% of theory)
Mass spectrum (ESI$^+$): m/z=363 [M+H]$^+$

EXAMPLE VII 1-(but-2-ynyl)-2-(3-tert-butoxycarbonylamino-piperidin-1-yl)-5-(naphth-1-ylmethylaminocarbonyl)-1H-imidazole 0.09 ml 1-aminomethylnaphthalene and 0.28 ml ethyldiisopropylamine are added to a solution of 0.20 g 2-(3-tert-butoxycarbonylamino-piperidin-1-yl)-3-(but-2-ynyl)-3H-imidazole-4-carboxylic acid and 0.19 g O-(benzotriazol-1-yl)-N,N,N',N'-tetramethyluronium tetrafluoroborate in 5 ml of dimethylformamide. The solution is stirred for 3 h at ambient temperature and then combined with saturated aqueous potassium carbonate solution. Then the mixture is extracted with ethyl acetate, the organic extracts are dried over sodium sulphate, and the solvent is removed. The residue is purified on silica gel (dichloromethane/methanol 1:0->7:3).

Yield: 0.18 g (65% of theory)
Mass spectrum (ESI$^+$): m/z=502 [M+H]$^+$

The following compounds are obtained analogously to Example VII:
(1) 1-(but-2-ynyl)-2-(3-tert-butoxycarbonylamino-piperidin-1-yl)-5-[N-(naphth-1-ylmethyl)-N-methyl-aminocarbonyl]-1H-imidazole
    Mass spectrum (ESI$^+$): m/z=516 [M+H]$^+$
(2) 1-(but-2-ynyl)-2-(3-tert-butoxycarbonylamino-piperidin-1-yl)-5-(phenanthridin-6-ylmethylaminocarbonyl)-1H-imidazole
    Mass spectrum (ESI$^+$): m/z=553 [M+H]$^+$
(3) 1-(but-2-ynyl)-2-(3-tert-butoxycarbonylamino-piperidin-1-yl)-5-(3-methylisoquinolin-1-ylmethylaminocarbonyl)-1H-imidazole
    Mass spectrum (ESI$^+$): m/z=517 [M+H]$^+$
(4) 1-(but-2-ynyl)-2-(3-tert-butoxycarbonylamino-piperidin-1-yl)-5-(quinolin-2-ylmethylaminocarbonyl)-1H-imidazole
    Mass spectrum (ESI$^+$): m/z=503 [M+H]$^+$
(5) 1-(but-2-ynyl)-2-(3-tert-butoxycarbonylamino-piperidin-1-yl)-5-(quinolin-3-ylmethylaminocarbonyl)-1H-imidazole
    Mass spectrum (ESI$^+$): m/z=503 [M+H]$^+$
(6) 1-(but-2-ynyl)-2-(3-tert-butoxycarbonylamino-piperidin-1-yl)-5-(2-phenyl-ethylaminocarbonyl)-1H-imidazole
    Mass spectrum (ESI$^+$): m/z=466 [M+H]$^+$

EXAMPLE VIII

2-Hydrazino-N-(naphth-1-ylmethyl)-2-oxo-acetamide 1.25 ml 1-aminomethylnaphthalene are added to a solution of 1.0 g methyl hydrazino-oxo-acetate in 10 ml of methanol. The solution is stirred for 16 h at ambient temperature and then some of the methanol is eliminated. The precipitate is separated off, washed with diethyl ether, and dried.

Yield: 1,77 g (86% of theory)
Mass spectrum (ESI$^+$): m/z=244 [M+H]$^+$

The following compounds are obtained analogously to Example VIII:
(1) 2-Hydrazino-N-(3-methyl-isoquinolin-1-ylmethyl)-2-oxo-acetamide
    Mass spectrum (ESI$^+$): m/z=259 [M+H]$^+$
    The reaction solution is heated to 60° C.
(2) 2-Hydrazino-2-oxo-N-(quinolin-6-ylmethyl)-acetamide
    Mass spectrum (ESI$^+$): m/z=245 [M+H]$^+$
(3) 2-Hydrazino-2-oxo-N-(phenanthridin-6-ylmethyl)-acetamide
    Mass spectrum (ESI$^+$): m/z=295 [M+H]$^+$
    The reaction is carried out in dimethylformamide in the presence of potassium carbonate at 40° C.

EXAMPLE IX 1-(naphth-1-ylmethylaminooxalyl)-4-benzyl-thiosemicarbazide 0.28 ml benzyl isothiocyanate are added to a solution of 0.5 g 2-hydrazino-N-naphth-1-ylmethyl-2-oxo-acetamide in 10 ml dioxane. Then the solvent is eliminated completely.

Yield: 0.84 g (99% of theory)
Mass spectrum (ESI$^+$): m/z=393 [M+H]$^+$

The following compounds are obtained analogously to Example IX:
(1) 1-(naphth-1-ylmethylaminooxalyl)-4-(3-methyl-but-2-enyl)-thiosemicarbazide
    Mass spectrum (ESI$^+$): m/z=371 [M+H]$^+$
(2) 1-[(3-methyl-isoquinolin-1-yl)methylaminooxalyl]-4-(but-2-ynyl)-thiosemicarbazide
    Mass spectrum (ESI$^+$): m/z=370 [M+H]$^+$
(3) 1-(naphth-1-ylmethylaminooxalyl)-4-(2-chloro-benzyl)-thiosemicarbazide
    Mass spectrum (ESI$^+$): m/z=427/429 (chlorine) [M+H]$^+$
(4) 1-(3-quinolin-6-ylmethylaminooxalyl)-4-(but-2-ynyl)-thiosemicarbazide
    Mass spectrum (ESI$^+$): m/z=356 [M+H]$^+$
(5) 1-(phenanthridin-6-ylmethylaminooxalyl]-4-(but-2-ynyl)-thiosemicarbazide
    Mass spectrum (ESI$^+$): m/z=406 [M+H]$^+$

EXAMPLE X 5-benzylamino-[1,3,4]oxadiazole-2-carboxylic acid-(naphth-1-ylmethyl)-amide A solution of 0.2 g 1-(naphth-1-ylmethylaminooxalyl)-4-benzyl-thiosemicarbazide in 5 ml dichloromethane is cooled in the ice bath. Then 45 μl methylsulphonyl chloride and 0.11 ml triethylamine are added. The solution is stirred for 3 h at ambient temperature and then diluted with 30 ml dichloromethane. After washing with aqueous sodium hydrogen carbonate solution the mixture is dried over sodium sulphate. After the solvent has been eliminated the crude product is obtained and is further reacted directly with piperazine (see Example 2(1)).

The following compounds are obtained analogously to Example X:
(1) 5-(3-methyl-but-2-enyl)amino-[1,3,4]oxadiazole-2-carboxylic acid-(naphth-1-ylmethyl)-amide
    Mass spectrum (ESI$^+$): m/z=337 [M+H]$^+$
(2) 5-(but-2-ynyl)amino-[1,3,4]oxadiazole-2-carboxylic acid-(3-methylisoquinolin-1-ylmethyl)-amide
    Mass spectrum (ESI$^+$): m/z=336 [M+H]$^+$
(3) 5-(2-chlorobenzyl)amino-[1,3,4]oxadiazole-2-carboxylic acid-(naphth-1-ylmethyl)-amide
    Mass spectrum (ESI$^+$): m/z=393/395 (chlorine) [M+H]$^+$
(4) 5-(but-2-ynyl)amino-[1,3,4]oxad iazole-2-carboxylic acid-(quinolin-6-ylmethyl)-amide
    Mass spectrum (ESI$^+$): m/z=322 [M+H]$^+$ (5) 5-(but-2-ynyl)amino-[1,3,4]oxadiazole-2-carboxylic acid-(phenanthridin-6-ylmethyl)-amide
Mass spectrum (ESI⁺): m/z=372 [M+H]⁺

EXAMPLE XI 3-(3-hydroxy-piperidin-1-yl)-4-(3-methyl-but-2-enyl)-5-(naphth-1-ylmethylaminocarbonyl)-4H-[1,2,4]triazole A mixture of 0.12 g 5-(3-methyl-but-2-enyl)amino-[1,3,4]oxadiazole-2-carboxylic acid-(naphth-1-ylmethyl)-amide and 1.80 g 3-hydroxypiperidine is stirred for 20 min at 200° C. in a microwave. After cooling to ambient temperature dichloromethane is added, the organic phase is washed once with water and once with 1 M hydrochloric acid, dried over sodium sulphate, and the solvent is removed.
Yield: 39 mg (26% of theory)
Mass spectrum (ESI⁺): m/z=420 [M+H]⁺
The following compounds are obtained analogously to Example XI:
(1) 3-(3-hydroxy-piperidin-1-yl)-4-benzyl-5-(naphth-1-ylmethylaminocarbonyl)-4H-[1,2,4]triazole
Mass spectrum (ESI⁺): m/z=442 [M+H]⁺
(2) 3-(3-hydroxy-piperidin-1-yl)-4-(but-2-ynyl)-5-(3-methyl-isoquinolin-1-ylmethylaminocarbonyl)-4H-[1,2,4]triazole
Mass spectrum (ESI⁺): m/z=419 [M+H]⁺
(3) 3-(3-hydroxy-piperidin-1-yl)-4-(2-chloro-benzyl)-5-(naphth-1-ylmethylaminocarbonyl)-4H-[1,2,4]triazole
Mass spectrum (ESI⁺): m/z=476/478 (chlorine) [M+H]⁺
(4) 3-(3-hydroxy-piperidin-1-yl)-4-(but-2-ynyl)-5-(quinolin-6-ylmethylaminocarbonyl)-4H-[1,2,4]triazole
Mass spectrum (ESI⁺): m/z=405 [M+H]⁺
(5) 3-(3-ethoxycarbonyl-piperidin-1-yl)-4-(but-2-ynyl)-5-(phenanthridin-6-ylmethylaminocarbonyl)-4H-[1,2,4]triazole
The reaction is carried out analogously, except that 3-ethoxycarbonylpiperidine is used instead of 3-hydroxypiperidine. The product is then further reacted directly (see Example 5)

EXAMPLE XII 3-(3-methylsulphonyloxy-piperidin-1-yl)-4-(2-chloro-benzyl)-5-(naphth-1-ylmethylaminocarbonyl)-4H-[1,2,4]triazole 0.11 ml triethylamine and 40 µl methylsulphonyl chloride are added to an ice-cooled suspension of 0.21 g 3-(3-hydroxy-piperidin-1-yl)-4-(2-chloro-benzyl)-5-(naphth-1-ylmethylaminocarbonyl)-4H-[1,2,4]triazole in 4 ml dichloromethane. The reaction mixture is stirred for 1 h in the ice bath and then for 1 h at ambient temperature. Then the mixture is diluted with dichloromethane and the organic phase is washed twice with 1 M hydrochloric acid and once with water. After drying on sodium sulphate the solvent is eliminated completely.
Yield: 0.24 g (99% of theory)
Mass spectrum (ESI⁺): m/z=554/556 (chlorine) [M+H]⁺
The following compounds are obtained analogously to Example XII:
(1) 3-(3-methylsulphonyloxy-piperidin-1-yl)-4-(but-2-ynyl)-5-(3-methyl-isoquinolin-1-ylmethylaminocarbonyl)-4H-[1,2,4]triazole
Mass spectrum (ESI⁺): m/z=497 [M+H]⁺
(2) 3-(3-methylsulphonyloxy-piperidin-1-yl)-4-(but-2-ynyl)-3-(quinolin-6-ylmethylaminocarbonyl)-4H-[1,2,4]triazole
Mass spectrum (ESI⁺): m/z=483 [M+H]⁺
Preparation of the final compounds:

EXAMPLE 1

1-(but-2-ynyl)-2-(3-amino-piperidin-1-yl)-5-(naphth-1-ylmethylaminocarbonyl)-1H-imidazole

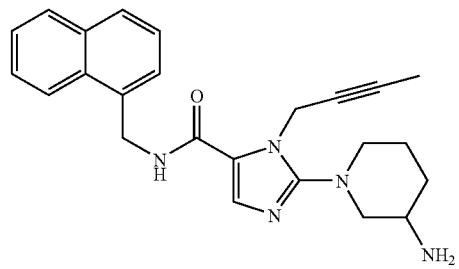

0.62 ml trifluoroacetic acid are added to a solution of 0.18 g 1-(but-2-ynyl)-2-(3-tert-butoxycarbonylamino-piperidin-1-yl)-5-(naphthyl-1-ylmethylaminocarbonyl)-1H-imidazole in 4 ml dichloromethane. After stirring for 3 h at ambient temperature the reaction solution is added to aqueous saturated potassium carbonate solution. The aqueous phase is extracted with dichloromethane, the combined organic phases are dried over sodium sulphate, and the solvent is removed. The residue is chromatographed on silica gel (dichloromethane/methanol 1:0->7:3).
Yield: 0.15 g (79% of theory)
Mass spectrum (ESI⁺): m/z=402 [M+H]⁺
The following compounds are obtained analogously to Example 1:
(1) 1-(but-2-ynyl)-2-(3-amino-piperidin-1-yl)-5-[N-(naphth-1-ylmethyl)-N-methylaminocarbonyl]-1H-imidazole
Mass spectrum (ESI⁺): m/z=416 [M+H]⁺

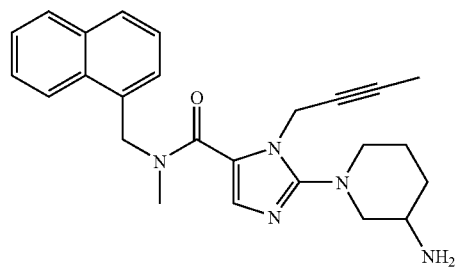

(2) 1-(but-2-ynyl)-2-(3-amino-piperidin-1-yl)-5-(phenanthridin-6-ylmethylaminocarbonyl)-1H-imidazole as trifluoroacetic acid salt
Mass spectrum (ESI⁺): m/z=453 [M+H]⁺

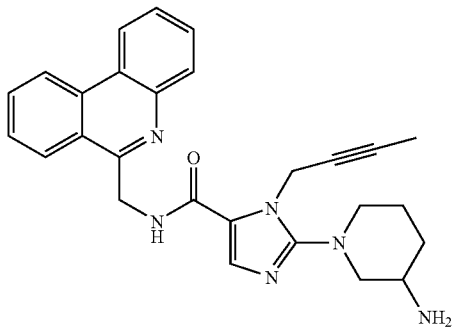

(3) 1-(but-2-ynyl)-2-(3-amino-piperidin-1-yl)-5-(3-methyl-isoquinolin-1-ylmethylaminocarbonyl)-1H-imidazole Mass spectrum (ESI⁺): m/z=417 [M+H]⁺

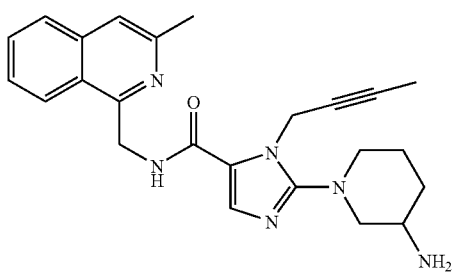

(4) 1-(but-2-ynyl)-2-(3-amino-piperidin-1-yl)-5-(quinolin-3-ylmethylaminocarbonyl)-1H-imidazole as trifluoroacetic acid salt Mass spectrum (ESI⁺): m/z=403 [M+H]⁺

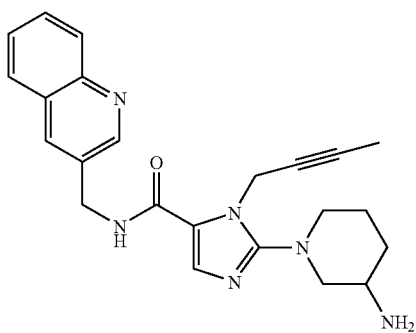

(5) 1-(but-2-ynyl)-2-(3-amino-piperidin-1-yl)-5-(2-phenyl-ethylaminocarbonyl)-1H-imidazole as trifluoroacetic acid salt Mass spectrum (ESI⁺): m/z=366 [M+H]⁺

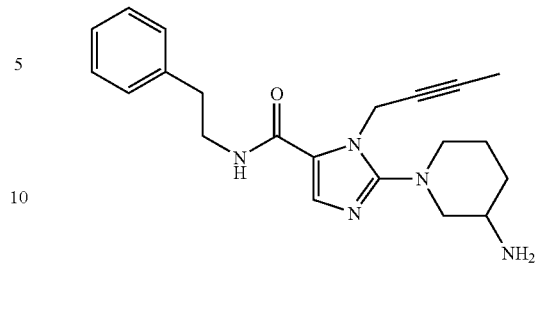

EXAMPLE 2

3-(piperazin-1-yl)-4-(3-methyl-but-2-enyl)-5-(naphth-1-ylmethylaminocarbonyl)-4H-[1,2,4]triazole

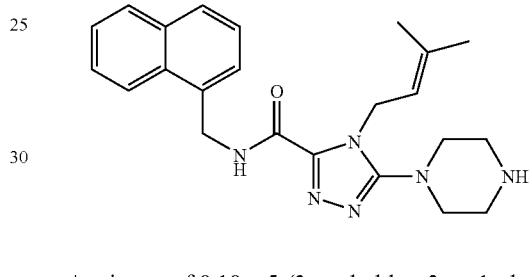

A mixture of 0.10 g 5-(3-methyl-but-2-en-1-ylamino)-[1,3,4]oxadiazole-2-carboxylic acid-(naphth-1-ylmethyl)-amide and 1.28 g piperazine is stirred for 15 min at 200° C. in a microwave. After cooling to ambient temperature dichloromethane is added, the organic phase is washed with water, dried over sodium sulphate and the solvent is removed. The residue is purified by chromatography on silica gel (dichloromethane/methanol 1:0->7:3).

Yield: 85 mg (71% of theory)

Mass spectrum (ESI⁺): m/z=405 [M+H]⁺

The following compounds are obtained analogously to Example 2:

(1) 3-(piperazin-1-yl)-4-benzyl-5-(naphth-1-ylmethylaminocarbonyl)-4H-[1,2,4]triazole Mass spectrum (ESI⁺): m/z=427 [M+H]⁺

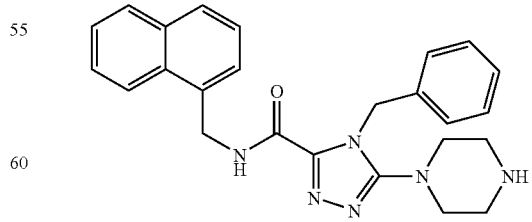

(2) 3-([1,4]diazepan-1-yl)-4-(3-methyl-but-2-enyl)-5-(naphth-1-ylmethylaminocarbonyl)-4H-[1,2,4]triazole Mass spectrum (ESI⁺): m/z=419 [M+H]⁺

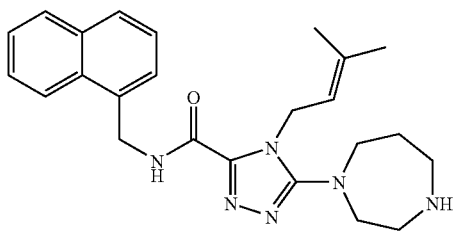

EXAMPLE 3

3-(3-amino-piperidin-1-yl)-4-(3-methyl-but-2-enyl)-
5-(naphth-1-ylmethylaminocarbonyl)-4H-[1,2,4]
triazole

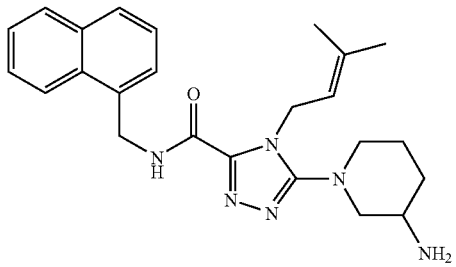

14 mg phthalimide, 65 mg triphenylphosphine and finally 50 μl of diisopropyl azodicarboxylate are added to a solution of 39 mg 3-(3-hydroxy-piperidin-1-yl)-4-(3-methyl-but-2-enyl)-5-(naphth-1-ylmethylaminocarbonyl)-4H-[1,2,4]triazole in 1 ml dry tetrahydrofuran. The solution is stirred for 14 h at ambient temperature and then evaporated to dryness. The residue is taken up in 2 ml of toluene and combined with 50 μl ethanolamine. After 4 h stirring at 80° C. the mixture is cooled to ambient temperature and the solvent is removed. The residue is purified by chromatography on silica gel (dichloromethane/methanol/ammonium hydroxide 95:5:1->80:20:1).

Yield: 3 mg (8% of theory)

Mass spectrum (ESI+): m/z=419 [M+H]+

The following compound is obtained analogously to Example 3:
(1) 3-(3-amino-piperidin-1-yl)-4-benzyl-5-(naphth-1-ylmethylaminocarbonyl)-4H-[1,2,4]triazole Mass spectrum (ESI+): m/z=441 [M+H]+

EXAMPLE 4

3-(3-amino-piperidin-1-yl)-4-(2-chloro-benzyl)-5-(naphth-1-ylmethylaminocarbonyl)-4H-[1,2,4]triazole 0.09 g sodium azide are added to a solution of 0.25 g 3-(3-hydroxy-piperidin-1-yl)-4-(2-chloro-benzyl)-5-(naphth-1-ylmethylaminocarbonyl)-4H-[1,2,4]triazole in 3 ml of dimethylformamide. The reaction mixture is stirred for 14 h at 110° C. After cooling to ambient temperature dichloromethane is added and the mixture is washed with water. The organic phase is dried over sodium sulphate and then the dichloromethane is removed. The residue is dissolved in 4 ml of tetrahydrofuran and combined with 0.7 ml 1 M trimethylphosphine solution in tetrahydrofuran. The reaction mixture is stirred for 16 h at ambient temperature and then diluted with dichloromethane. The organic phase is washed with water and aqueous saturated sodium hydrogen carbonate solution, dried over sodium sulphate and freed from the solvent. The residue is purified by chromatography on silica gel (dichloromethane/methanol/ammonium hydroxide 95:5:1->80:20:1).

Yield: 77 mg (36% of theory)

Mass spectrum (ESI+): m/z=475/477 (chlorine) [M+H]+

The following compounds are obtained analogously to Example 4:
(1) 3-(3-amino-piperidin-1-yl)-4-(but-2-ynyl)-5-(3-methyl-isoquinolin-1-ylmethylaminocarbonyl)-4H-[1,2,4]triazole Mass spectrum (ESI+): m/z=418 [M+H]+

(2) 3-(3-amino-piperidin-1-yl)-4-(but-2-ynyl)-5-(quinolin-6-ylmethylaminocarbonyl)-4H-[1,2,4]triazole Mass spectrum (ESI+): m/z=404 [M+H]+

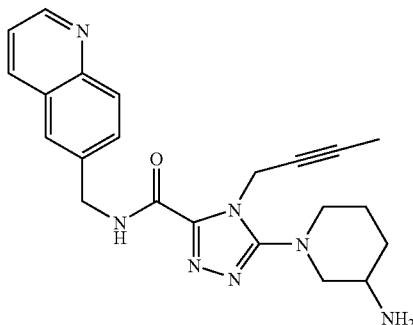

EXAMPLE 5

3-(3-amino-piperidin-1-yl)-4-(but-2-ynyl)-5-(phenanthridin-6-ylmethylaminocarbonyl)-4H-[1,2,4]triazole

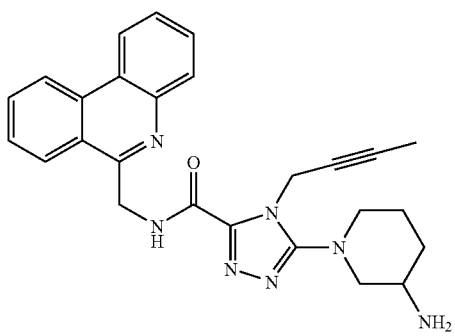

A solution of 0.15 g 3-(3-ethoxycarbonyl-piperidin-1-yl)-4-(but-2-ynyl)-5-(phenanthridin-6-ylmethylaminocarbonyl)-4H-[1,2,4]triazole in 0.5 ml sodium hydroxide solution and 1 ml of tetrahydrofuran is stirred for 2 h at 45° C. Then the solution is acidified with 2 M hydrochloric acid and extracted with ethyl acetate. The organic extracts are dried over sodium sulphate and the solvent is eliminated completely. The residue is dissolved in 3 ml 1,2-dichloroethane. 0.12 ml triethylamine and 0.08 ml diphenylphosporylazide are added to the solution. Then the solution is stirred for 2 h at 80° C. After cooling to ambient temperature it is diluted with dichloromethane and washed once each with 1 M sodium hydroxide solution and aqueous sodium hydrogen carbonate solution. The organic phase is dried over sodium sulphate and the solvent is eliminated. The residue is dissolved in 1 ml of tetrahydrofuran and treated with 1 ml 1 M sodium hydroxide solution. After 1 h stirring aqueous sodium hydrogen carbonate solution is added, the mixture is extracted with dichloromethane and dried over sodium sulphate. The residue is purified by chromatography on silica gel (dichloromethane/methanol/ammoniumhydroxid 98:2:1->80:20:1).

Yield: 22 mg (16% of theory)

Mass spectrum (ESI$^+$): m/z=454 [M+H]$^+$

The following compounds may also be obtained analogously to the foregoing Examples and other methods known from the literature:

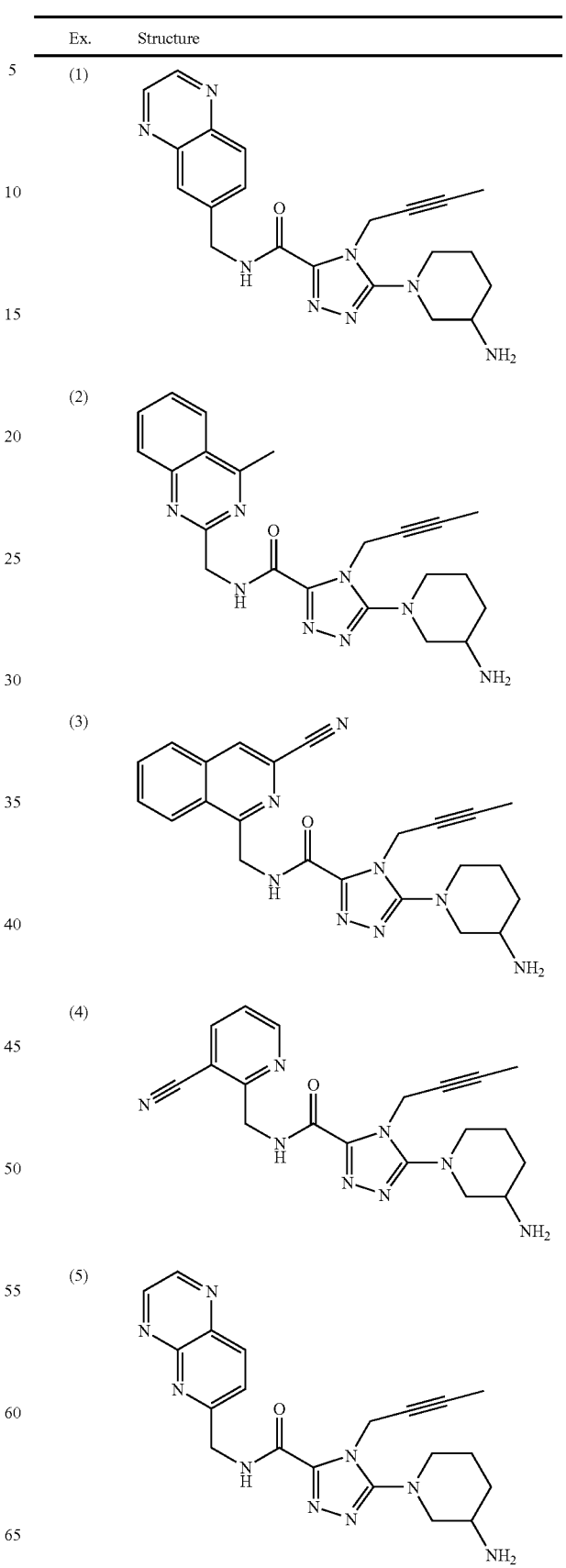

| Ex. | Structure |
|---|---|
| (6) | 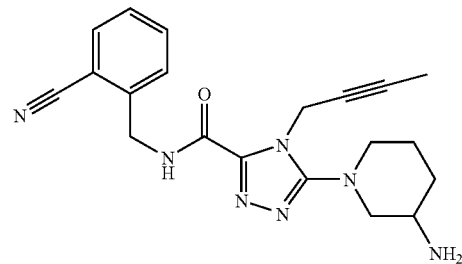 |
| (7) | 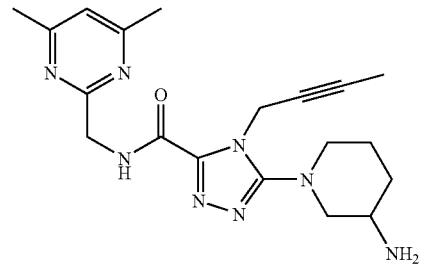 |
| (8) | 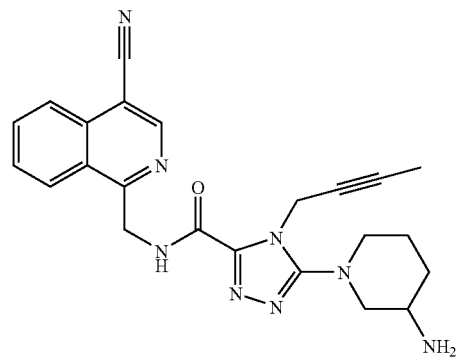 |
| (9) | 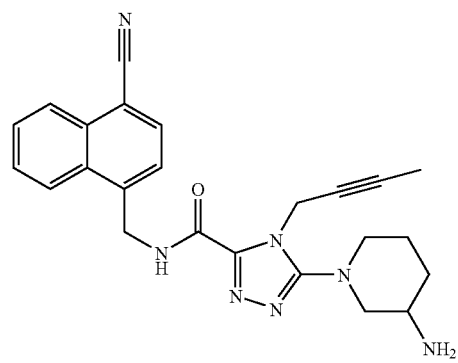 |
| Ex. | Structure |
|---|---|
| (10) | 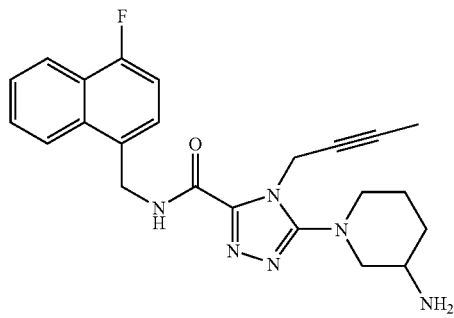 |
| (11) | 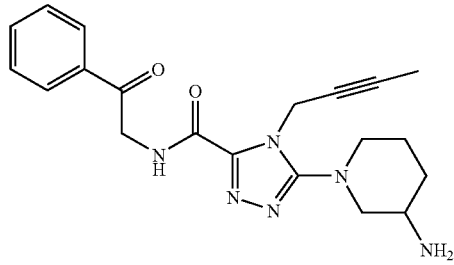 |
| (12) | 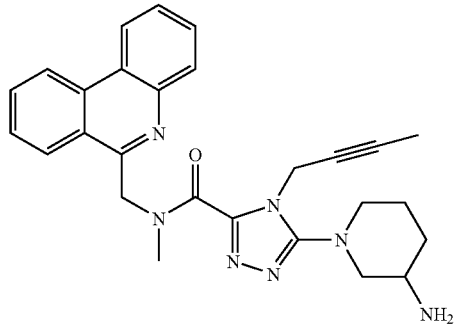 |
| (13) | 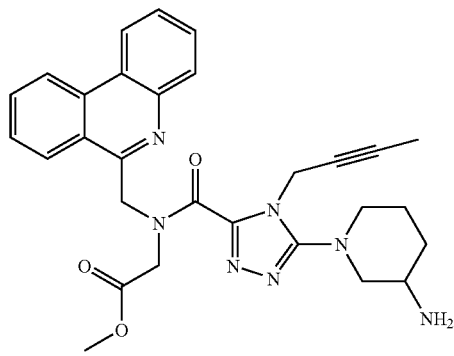 |

| Ex. | Structure |
|---|---|
| (14) | 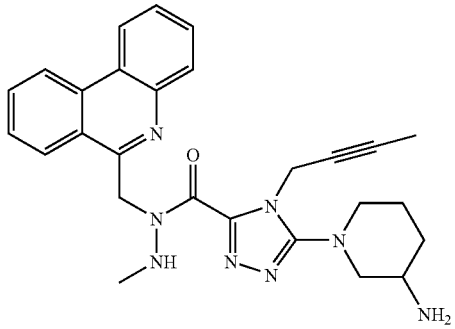 |
| (15) | 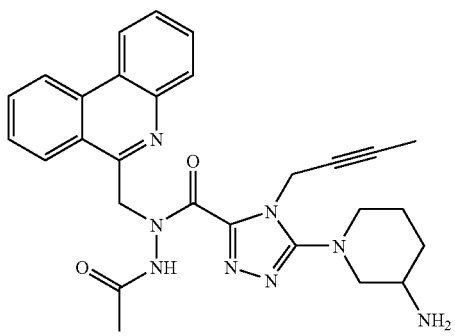 |
| (16) | 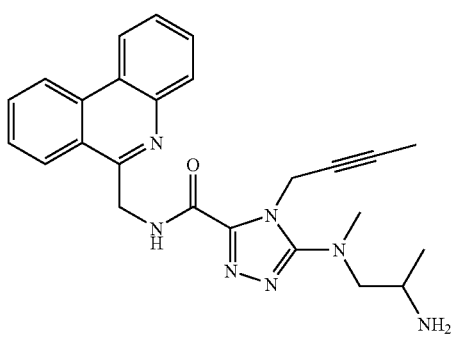 |
| (17) | 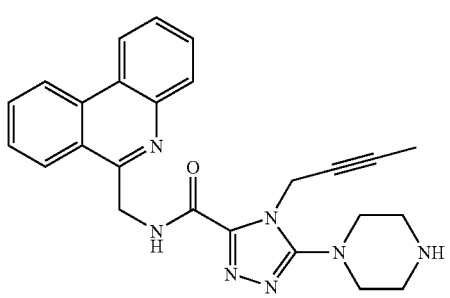 |
| Ex. | Structure |
|---|---|
| (18) | 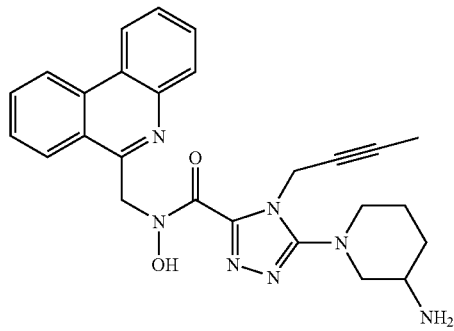 |
| (19) | 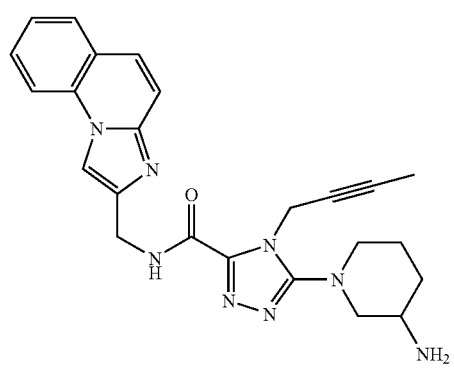 |
| (20) | 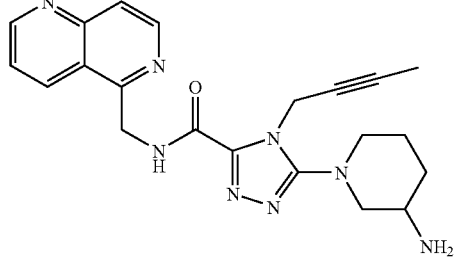 |
| (21) | 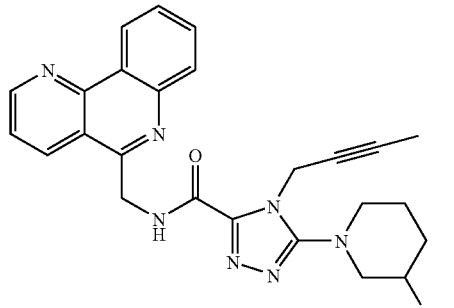 |
| (22) | 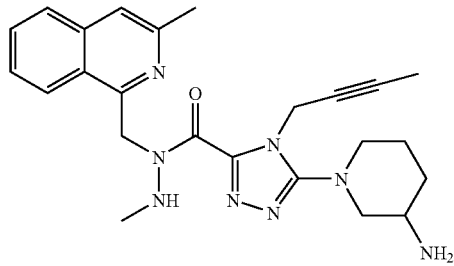 |

| Ex. | Structure |
|---|---|
| (23) | 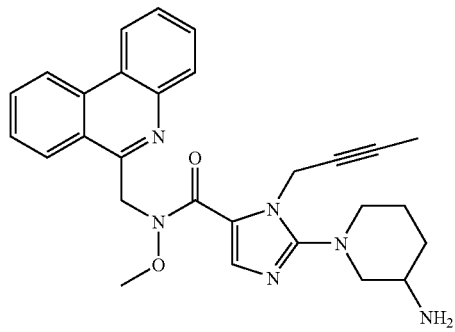 |
| (24) | 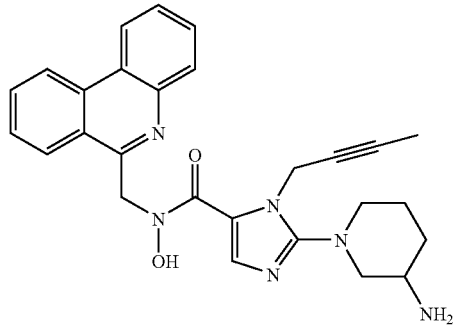 |
| (25) | 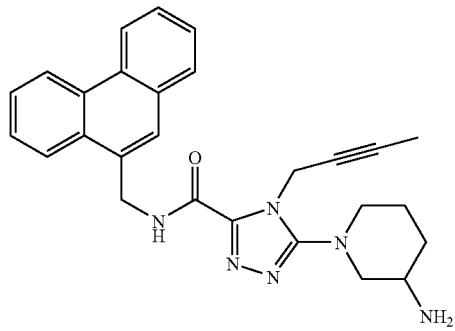 |
| (26) | 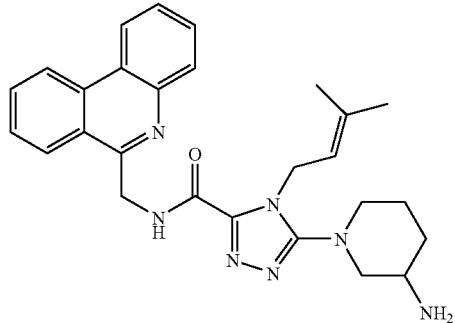 |
| Ex. | Structure |
|---|---|
| (27) | 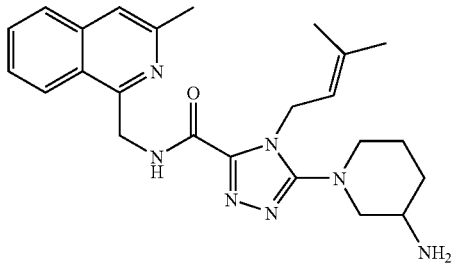 |
| (28) | 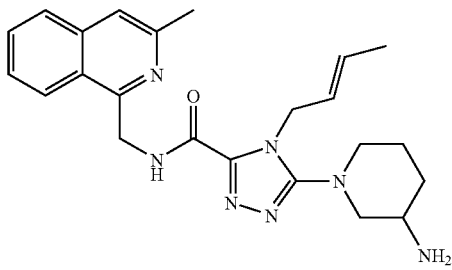 |
| (29) | 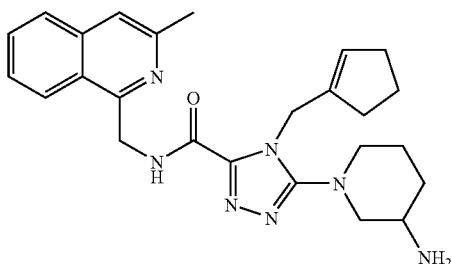 |
| (30) | 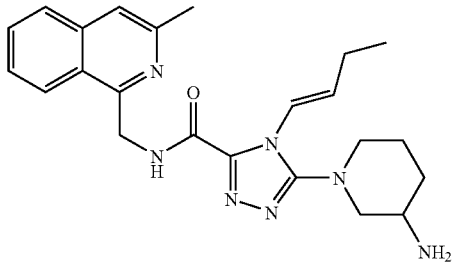 |
| (31) | 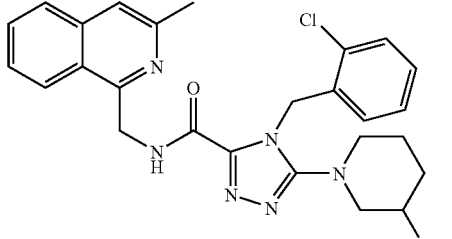 |

| Ex. | Structure |
|---|---|
| (32) | 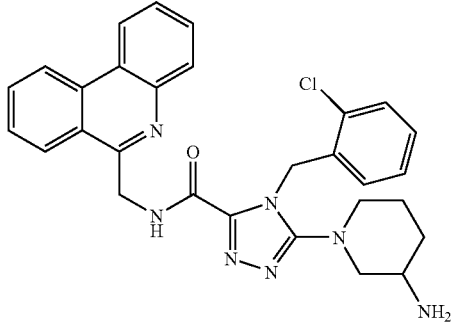 |
| (33) | 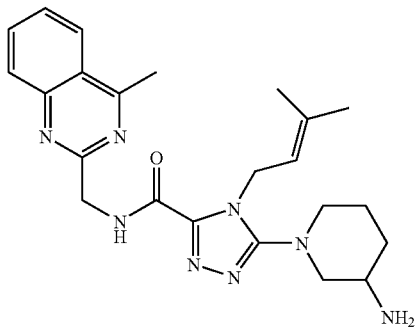 |
| (34) | 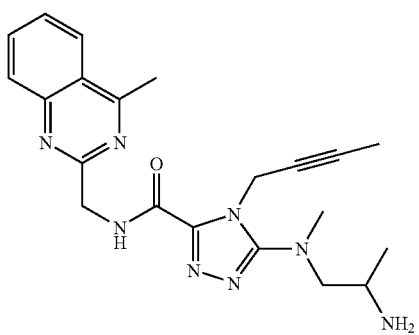 |
| (35) | 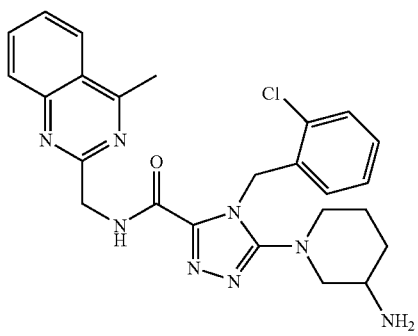 |

| Ex. | Structure |
|---|---|
| (36) | 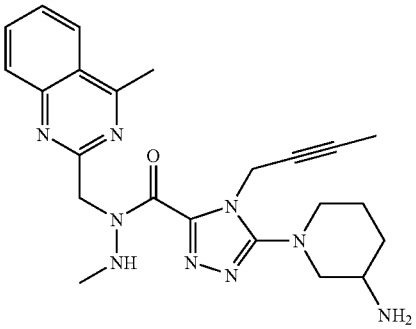 |

EXAMPLE 6

Coated tablets containing 75 mg of active substance

| 1 tablet core contains: | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks about 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 7

Tablets containing 100 mg of active substance

| Composition: 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Preparation:

The active substance, lactose, and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE 8

Tablets containing 150 mg of active substance

| Composition: 1 tablet contains: | |
|---|---:|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm.

The granules, dried at 45° C., are passed through the same screen again and mixed with the specified amount of magnesium stearate. Tablets are pressed from the mixture.

Weight of tablet: 300 mg die: 10 mm, flat

EXAMPLE 9

Hard gelatine capsules containing 150 mg of active substance

| 1 capsule contains: | |
|---|---:|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE 10

Suppositories containing 150 mg of active substance

| 1 suppository contains: | |
|---|---:|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 11

Suspension containing 50 mg of active substance

| 100 ml of suspension contain: | |
|---|---:|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution, and the flavoring have been added and dissolved, the suspension is evacuated with stirring to eliminate air.

5 ml of suspension contain 50 mg of active substance.

EXAMPLE 12

Ampoules containing 10 mg active substance

| Composition: | |
|---|---:|
| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile, and transferred into 2 ml ampoules.

EXAMPLE 13

Ampoules containing 50 mg of active substance

| Composition: | |
|---|---|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile, and transferred into 10 ml ampoules.

We claim:

1. A compound of formula (I):

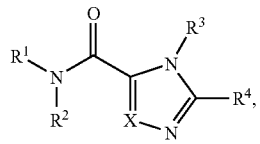

wherein $R^1$ denotes an aryl-$C_{1-6}$-alkyl or heteroaryl-$C_{1-6}$-alkyl group wherein each methylene group of the alkyl group may be substituted by one or two fluorine atoms or a $C_{1-3}$-alkyl group and a methylene group may be replaced by a carbonyl group, or an aryl-$C_{2-6}$-alkenyl or heteroaryl-$C_{2-6}$-alkenyl group, wherein the alkenyl chain may be substituted by 1 to 10 fluorine atoms or a cyano, $C_{1-3}$-alkyloxy-carbonyl, $C_{1-3}$-alkyl or nitro group, $R^2$ denotes a hydrogen atom, a $C_{1-6}$-alkyl group, a $C_{1-6}$-alkyl group substituted by a group $R_a$, where $R_a$ denotes a fluorine, chlorine or bromine atom, or a trifluoromethyl, nitro, aryl, heteroaryl, cyano, carboxy, $C_{1-4}$-alkoxy-carbonyl, aminocarbonyl, $C_{1-4}$-alkylamino-carbonyl, di-($C_{1-3}$-alkyl)-amino-carbonyl, pyrrolidin-1-ylcarbonyl, piperidin-1-ylcarbonyl, morpholin4-ylcarbonyl, piperazin-1-ylcarbonyl, 4-($C_{1-4}$-alkyl)-piperazin-1-ylcarbonyl, $C_{1-4}$-alkylcarbonyl, arylcarbonyl, heteroarylcarbonyl, $C_{1-3}$-alkylsulphinyl or $C_{1-3}$-alkylsulphonyl group, a $C_{2-6}$-alkyl group substituted from position 2 by a group $R_b$, where $R_b$ denotes a hydroxy, $C_{1-3}$-alkoxy, amino, $C_{1-3}$-alkylamino, di-($C_{1-3}$-alkyl)-amino, pyrrolidin-1-yl, piperidin-1-yl, morpholin4-yl, piperazin-1-yl or 4-($C_{1-4}$-alkyl)-piperazin-1-yl group, an NH group substituted by a group $R_c$, where $R_c$ denotes a $C_{1-6}$-alkyl, $C_{2-6}$-alkenyl, aryl, heteroaryl, $C_{1-4}$-alkoxy-carbonyl, amino-carbonyl, $C_{1-4}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-($C_{1-4}$-alkyl)-piperazin-1-ylcarbonyl, $C_{1-4}$-alkyl-carbonyl, aryl-carbonyl, heteroarylcarbonyl, $C_{1-3}$-alkylsulphinyl or $C_{1-3}$-alkylsulphonyl group, a hydroxy group, a $C_{1-4}$-alkoxy group, or a $C_{2-6}$-alkenyl or $C_{2-6}$-alkynyl group, X denotes a nitrogen atom or a CH group, $R^3$ denotes a $C_{5-7}$-cycloalkenylmethyl group optionally substituted by a $C_{1-3}$-alkyl group, an arylmethyl or heteroarylmethyl group, a straight-chain or branched $C_{2-8}$-alkenyl group that may be substituted by 1 to 15 fluorine atoms or a cyano, nitro or $C_{1-3}$-alkoxy-carbonyl group, or a straight-chain or branched $C_{3-6}$-alkynyl group that may be substituted by 1 to 9 fluorine atoms or a cyano, nitro or $C_{2-8}$-alkoxy-carbonyl group, and $R^4$ denotes a pyrrolidin-1-yl or azetedin-1-yl group which is substituted in the 3 position by an amino or $C_{1-3}$-alkylamino group and may additionally be substituted by one or two $C_{1-3}$-alkyl groups, a piperidin-1-yl or hexahydroazepin-1-yl group which is substituted in the 3 position or in the 4 position by an amino group or $C_{1-3}$-alkylamino group and may additionally be substituted by one or two $C_{1-3}$-alkyl groups, a piperazin-1-yl or homopiperazin-1-yl group which may be substituted by one or two $C_{1-3}$-alkyl groups, an amino group substituted by the groups $R^{15}$ and $R^{16}$ wherein $R^{15}$ denotes a hydrogen atom, a $C_{1-6}$-alkyl, $C_{3-6}$-cycloalkyl, $C_{3-6}$-cycloalkyl-$C_{1-3}$-alkyl, aryl or aryl-$C_{1-3}$-alkyl group, and $R^{16}$ denotes a $R^{17}$—$C_{2-3}$-alkyl group, wherein the $C_{2-3}$-alkyl moiety is straight-chained and may be substituted by 1 to 4 $C_{1-3}$-alkyl groups, which may be identical or different, and the $C_{2-3}$-alkyl group may be linked to $R^{17}$ from position 2, and $R^{17}$ denotes an amino or $C_{1-3}$-alkylamino group, an amino group substituted by the groups $R^{15}$ and $R^{18}$ wherein $R^{18}$ denotes a $C_{3-10}$-cycloalkyl-$C_{1-2}$-alkyl- group substituted by $R^{19}$ in the 1 position of the cycloalkyl group or a $C_{3-10}$-cycloalkyl group substituted in the 1 or 2 position by a $R^{19}$—$C_{1-2}$-alkyl group, wherein $R^{19}$ denotes an amino or $C_{1-3}$-alkylamino group, an amino group substituted by the groups $R^{15}$ and $R^{20}$ wherein $R^{20}$ denotes a $C_{4-10}$-cycloalkyl or $C_{4-10}$-cycloalkyl-methyl group wherein a methylene group of the $C_{4-10}$-cycloalkyl group is replaced by an —NH— group, or an amino group substituted by the groups $R^{15}$ and $R^{21}$ wherein $R^{21}$ denotes a $C_{3-10}$-cycloalkyl group substituted in the 2 or 3 position by an amino or $C_{1-3}$-alkylamino group, while the above-mentioned groups $R^{18}$, $R^{20}$ and $R^{21}$ may be mono- or disubstituted by $R_d$, while the substituents may be identical or different, and $R_d$ denotes a fluorine atom, a $C_{1-3}$-alkyl, trifluoromethyl, cyano, amino, $C_{1-3}$-alkylamino, hydroxy or $C_{1-3}$-alkyloxy group, and wherein one or two methylene groups of the cycloalkyl group may each be replaced independently of one another by an oxygen or sulphur atom or by an —NH— or —N($C_{1-3}$-alkyl)- group, or by a carbonyl, sulphinyl or sulphonyl group, while by the aryl groups mentioned in the definition of the above groups are meant phenyl or naphthyl groups, which may be mono-, di- or trisubstituted independently of one another by $R_h$, where the substituents may be identical or different and $R_h$ denotes a fluorine, chlorine, bromine or iodine atom, a trifluoromethyl, cyano, nitro, amino, aminocarbonyl, $C_{1-3}$-alkoxy-carbonyl, aminosulphonyl, methylsulphonyl, acetylamino, methylsulphonylamino, $C_{1-3}$-alkyl, cyclopropyl, ethenyl, ethynyl, morpholinyl, hydroxy, $C_{1-3}$-alkyloxy, difluoromethoxy or trifluoromethoxy group, and wherein additionally each hydrogen atom may be replaced by a fluorine atom, by the heteroaryl groups mentioned in the definition of the above-mentioned groups are meant:

a pyrrolyl, furanyl, thienyl, pyridyl, indolyl, benzofuranyl, benzothiophenyl, phenanthridinyl, quinolinyl or isoquinolinyl group, or a pyrrolyl, furanyl, thienyl or pyridyl group, wherein one or two methyne groups are replaced by nitrogen atoms, or an indolyl, benzofuranyl, benzothiophenyl, phenanthridinyl, quinolinyl or isoquinolinyl group, wherein one to three methyne groups are replaced by nitrogen atoms, or a 1,2-dihydro-2-oxo-pyridinyl, 1,4-dihydro-4-oxo-pyridinyl, 2,3-dihydro-3-oxo-pyridazinyl, 1,2,3,6-tetrahydro-3,6-dioxo-pyridazinyl, 1,2-dihydro-2-oxo-pyrimidinyl, 3,4-dihydro-4-oxo-pyrimidinyl, 1,2,3,4-tetrahydro-2,4-dioxo-pyrimidinyl, 1,2-dihydro-2-oxo-pyrazinyl, 1,2,3,4-tetrahydro-2,3-dioxo-pyrazinyl, 2,3-dihydro-2-oxo-indolyl, 2,3-dihydrobenzofuranyl, 2,3-dihydro-2-oxo-1H-benzimidazolyl, 2,3-dihydro-2-oxo-benzoxazolyl, 1,2-dihydro-2-oxo-quinolinyl, 1,4-dihydro-4-oxo-quinolinyl, 1,2-dihydro-1-oxo-isoquinolinyl, 1,4-dihydro-4-oxo-cinnolinyl, 1,2-dihydro-2-oxo-quinazolinyl, 3,4-dihydro-4-oxo-quinazolinyl, 1,2,3,4-tetrahydro-2,4-dioxo-quinazolinyl, 1,2-dihydro-2-oxoquinoxalinyl, 1,2,3,4-tetrahydro-2,3-dioxo-quinoxalinyl, 1,2-dihydro-1-oxo-phthalazinyl, 1,2,3,4-tetrahydro-1,4-dioxo-phthalazinyl, chromanyl, cumarinyl, 2,3-dihydro-benzo[1,4]dioxinyl or 3,4-dihydro-3-oxo-2H-benzo[1,4]oxazinyl group, and the above-mentioned heteroaryl groups may be mono- or disubstituted by $R_h$, while the substituents may be identical or different and $R_h$ is as hereinbefore defined, by the cycloalkyl groups mentioned in the definition of the above-mentioned groups are meant both monocyclic and polycyclic ring systems, while the polycycles may be anellated, spiro-linked or bridged in structure, for example the term polycyclic groups denotes decalin, octahydroindene, norbornane, spiro[4.4]nonane, spiro[4.5]decane, bicyclo[2.1.1]hexane, bicyclo[2.2.2]octane, bicyclo[3.2.1]octane, bicyclo[3.2.2]nonane, bicyclo[3.3.1]nonane, bicyclo[3.3.2]decane or adamantane, while, unless otherwise stated, the above-mentioned alkyl, alkenyl and alkynyl groups may be straight-chain or branched, a tautomers, enantiomers, or diastereomers thereof, or a mixture thereof, or a physiologically acceptable salt thereof.

2. The compound according to claim 1, wherein
X denotes a nitrogen atom or a CH group,
$R^3$ denotes a 1-buten-1-yl, 2-buten-1-yl, 3-methyl-2-buten-1-yl, 2-butyn-1-yl, cyclopent-1-enyl-methyl, furanylmethyl, thienylmethyl, chlorobenzyl, bromobenzyl, iodobenzyl, methoxybenzyl or cyanobenzyl group, and $R^4$ denotes
an N-(2-aminoethyl)-N-methyl-amino group which may be substituted in the ethyl moiety by one or two $C_{1-3}$-alkyl groups, or
a 3-aminopiperidin-1-yl, piperazin-1-yl or [1,4]diazepan-1-yl group, while the above-mentioned groups may each additionally be substituted by one or two $C_{1-3}$-alkyl groups, or an enantiomer or diastereomers thereof, or a mixture thereof or a physiologically acceptable salt thereof.

3. The compound according to claim 1, wherein
$R^1$ denotes a phenylmethyl, phenylcarbonylmethyl, phenylprop-2-enyl, pyridinylmethyl, pyrimidinylmethyl, naphthylmethyl, quinolinylmethyl, isoquinolinylmethyl, quinazolinylmethyl, quinoxalinylmethyl, phenanthridinylmethyl, naphthyridinylmethyl or benzotriazolylmethyl group, while all the above-mentioned aryl and heteroaryl groups may be substituted by one or two fluorine, chlorine or bromine atoms or one or two cyano, nitro, amino, $C_{1-3}$-alkyl, $C_{1-3}$-alkyloxy or morpholinyl groups, while the substituents are identical or different, $R^2$ denotes a hydrogen atom or a methyl group,
X denotes a nitrogen atom or a CH group,
$R^3$ denotes a 1-buten-1-yl, 2-buten-1-yl, 3-methyl-2-buten-1-yl, 2-butyn-1-yl, cyclopent-1-enyl-methyl, furanylmethyl, thienylmethyl, benzyl, chlorobenzyl, bromobenzyl, iodobenzyl or cyanobenzyl group and $R^4$ denotes an N-(2-aminoethyl)-N-methylamino, N-(2-aminopropyl)-N-methyl-amino, 3-aminopiperidin-1-yl, piperazin-1-yl or [1,4]diazepan-1-yl group, or an enantiomer or diastereomer thereof, or a mixture thereof or a physiologically acceptable salt thereof.

4. The compound according to claim 1, wherein
$R^1$ denotes a phenylethyl, naphthylmethyl, methylisoquinolinylmethyl, quinolinylmethyl or phenanthridinylmethyl group,
$R^2$ denotes a hydrogen atom or a methyl group,
X denotes a nitrogen atom or a CH group,
$R^3$ denotes a 3-methyl-2-buten-1-yl, 2-butyn-1-yl, benzyl or 2-chlorobenzyl group and
$R^4$ denotes a 3-aminopiperidin-1-yl, [1,4]diazepan-1-yl or piperazin-1-yl group, or an enantiomer or diastereomer thereof, or a mixture thereof or a physiologically acceptable salt thereof.

5. The compound according to claim 1, wherein $R^4$ denotes a 3-aminopiperidin-1-yl group, or a tautomer, enantiomer, or diastereomer thereof, or a mixture thereof, or a physiologically acceptable salt thereof.

6. The compound according to claim 1, wherein X denotes a nitrogen atom, or a tautomers, enantiomers, or diastereomer thereof, or a mixture thereof, or a physiologically acceptable salt thereof.

7. The compound according to claim 1, wherein X denotes a CH group, or a tautomer, enantiomer, or diastereomer thereof, or a mixture thereof, or a physiolgically acceptable salt thereof.

8. The compound according to claim 1 selected from the group consisting of:

(1) 1-(but-2-ynyl)-2-(3-amino-piperidin-1-yl)-5-(naphth-1-ylmethylaminocarbonyl)-1H-imidazole;

(2) 1-(but-2-ynyl)-2-(3-amino-piperidin-1-yl)-5-[N-(naphth-1-ylmethyl)-N-methyl-amino-carbonyl]-1H-imidazole;

(3) 1-(but-2-ynyl)-2-(3-amino-piperidin-1-yl)-5-(phenanthridin-6-ylmethylamino-carbonyl)-1H-imidazole;

(4) 1-(but-2-ynyl)-2-(3-amino-piperidin-1-yl)-5-(3-methyl-isoquinolin-1-ylmethylamino-carbonyl)-1H-imidazole;

(5) 1-(but-2-ynyl)-2-(3-amino-piperidin-1-yl)-5-(quinolin-3-ylmethylaminocarbonyl)-1H-imidazole;

(6) 1-(but-2-ynyl)-2-(3-amino-piperidin-1-yl)-5-(2-phenyl-ethylaminocarbonyl)-1H- imidazole (7) 3-(piperazin-1-yl)-4-(3-methyl-but-2-enyl)-5-(naphth-1-ylmethylaminocarbonyl)-4H- [1,2,4]triazole;

(8) 3-(piperazin-1-yl)-4-benzyl-5-(naphth-1-ylmethylaminocarbonyl)-4H-[1,2,4]triazole;

(9) 3-([1,4]diazepan-1-yl)-4-(3-methyl-but-2-enyl)-5-(naphth-1-ylmethylaminocarbonyl)-4H-[1,2,4]triazole;

(10) 3-(3-amino-piperidin-1-yl)-4-(3-methyl-but-2-enyl)-5-(naphth-1-ylmethylaminocarbonyl)-4H-[1,2,4]triazole;

(11) 3-(3-amino-piperidin-1-yl)-4-benzyl-5-(naphth-1-ylmethylaminocarbonyl)-4H-[1,2,4]triazole;

(12) 3-(3-amino-piperidin-1-yl)-4-(2-chloro-benzyl)-5-(naphth-1-ylmethylamino-carbonyl)-4H-[1,2,4]triazole;

(13) 3-(3-amino-piperidin-1-yl)-4-(but-2-ynyl)-5-(3-methyl-isoquinolin-1-ylmethylamino-carbonyl)-4H-[1,2,4]triazole;

(14) 3-(3-amino-piperidin-1-yl)-4-(but-2-ynyl)-5-(quinolin-6-ylmethylaminocarbonyl)-4H-[1,2,4]triazole; and

(15) 3-(3-amino-piperidin-1-yl)-4-(but-2-ynyl)-5-(phenanthridin-6-ylmethylamino-carbonyl)-4H-[1,2,4]triazole;

or a physiologically acceptable salt thereof.

9. A pharmaceutical composition comprising the compound according to claim 1 and one or more inert carriers or diluents.

10. A process for preparing the compound according to claim 1, comprising
reacting a compound of formula II

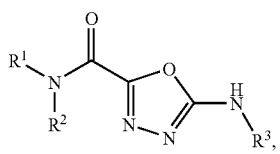
(II)

wherein $R^1$ to $R^3$ are defined as in claim 1, with a compound of general formula III

H—$R^4$    (III), wherein $R^4$ is defined as in claim 1.

11. A process for preparing the compound according to claim 1, comprising
diazotizing and then reducing a compound of formula IV

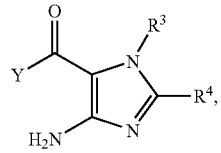
(IV)

wherein Y denotes a $C_{1-6}$-alkoxy, di-($C_{1-4}$-alkyl)-amino, or —$NR^1R^2$ group, wherein $R^1$ is defined as in claim 1 and $R^2$ is defined as in claim 1, with the exception of the hydrogen atom, and $R^3$ and $R^4$ are defined as in claim 1.

12. The process according to claim 11, wherein the group Y is converted into the group —$NR^1R^2$, wherein $R^1$ and $R^2$ are defined as in claim 1.

13. A process for preparing the compound according to claim 1, comprising
deprotecting a compound of formula V

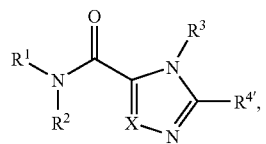
(V)

wherein $R^1$, $R^2$, X and $R^3$ are defined as in claim 1 and $R^{4'}$ contains an N-tert.-butyloxycarbonylamino, N-tert.-butyloxycarbonyl-N-alkylamino, phthalimido or azido group, while the alkyl moiety of the N-tert.-butyloxycarbonyl-N-alkylamino group may be substituted as mentioned in claim 1.

14. The process according to claim 13, wherein the compound thus obtained is converted by acylation or sulphonylation into a corresponding acyl or sulphonyl compound of formula I.

15. The process according to claim 13, wherein the compound thus obtained is converted by alkylation or reductive alkylation into a corresponding alkyl compound of formula I.

16. The process according to claim 13, wherein the compound thus obtained is converted by esterification into a corresponding ester of formula I.

17. The process according to claim 13, wherein the compound thus obtained is converted by reaction with an amine into a corresponding amide of formula I.

* * * * *